US 7,674,457 B2

(12) United States Patent
Borlongan et al.

(10) Patent No.: US 7,674,457 B2
(45) Date of Patent: Mar. 9, 2010

(54) METHODS FOR ENHANCING NEUROPROTECTION VIA ADMINISTRATION OF STEM CELLS AND BLOOD BRAIN BARRIER PERMEABILIZERS

(75) Inventors: Cesario V Borlongan, Augusta, GA (US); Paul R. Sanberg, Tampa, FL (US)

(73) Assignee: University of South Florida, Tampa, FL (US)

( * ) Notice: Subject to any disclaimer, the term of this patent is extended or adjusted under 35 U.S.C. 154(b) by 386 days.

(21) Appl. No.: 11/012,849

(22) Filed: Dec. 15, 2004

(65) Prior Publication Data

US 2005/0169902 A1 Aug. 4, 2005

Related U.S. Application Data

(60) Provisional application No. 60/531,227, filed on Dec. 19, 2003, provisional application No. 60/529,689, filed on Dec. 15, 2003.

(51) Int. Cl.
*A61K 35/14* (2006.01)
*A61K 31/047* (2006.01)

(52) U.S. Cl. .................................... 424/93.7

(58) Field of Classification Search ....................... None
See application file for complete search history.

(56) References Cited

U.S. PATENT DOCUMENTS

| | | | |
|---|---|---|---|
| 2001/0038836 A1* | 11/2001 | During et al. | 424/93.7 |
| 2002/0028510 A1* | 3/2002 | Sanberg et al. | 435/368 |
| 2004/0197310 A1* | 10/2004 | Sanberg et al. | 424/93.7 |
| 2006/0159666 A1* | 7/2006 | Willing et al. | 424/93.7 |

OTHER PUBLICATIONS

Kipnis 2002. Trends in Molecular Medicine 8:319-323.*
Sawa et al. (2003. Molecular Medicin 9:3-9.*
Lobel 2003. Experimental Neurology 181:97-98, Tenth Annual Conference of the American Society for Neural Transplantation & Repair, Clearwater, FL May 1-4, 2003.*
Borlongan 2002. Brain Research 956:211-220.*
Current Protocols in Cytometry 1999, pp. A.2A.1-A.2A.4.*
Kreek et al. 2002. Nature Reviews Drug Discovery 1:710-726.*
Volkmar 2003. The Lancet 362:1133-1141.*
Guidotti 1998. Human Molecular Genetics 7:831-838.*
Tsuboi 1973 Cancer Research 33:1326-1330.*
Hatanka 1973 (Proc Natl Acad Sci USA 70(5):1364-1367).*
Joint FAO/WHO Expert Committee on Food Additives Oct. 11-18, 1966.*
Steiner 2001 (Neurology 57 (Suppl 2):S61-S68).*
Bicknese, et al., 2002, "Human Umbilical Cord Blood Cell can be Induced to Express Markers for Neurons and Glia", Cell Transplantation, 11:261-264.
Borlongan, et al., 2004, "Central nervous system entry of peripherally injected umbilical cord blood cells is not required for neuroprotection in stroke", Stroke, 35(10):2385-9.
Broxmeyer et al., 1992, "Growth Characteristics and Expansion of Human Umbilical Cord Blood and Estimation of its Potential for Transplantation in Adults", Proc. Natl. Acad. Sci. USA, 89:4109-4113.
Broxmeyer, 1995, "Questions to be Answered Regarding Umbilical Cord Blood Hematopoietic Stem and Progenitor Cells and their use in Transplantation", Transfusion, 35:694-702.
Chen et al., 2001, "Intravenous Administration of Human Umbilical Cord Blood Reduces Behavioral Deficits After Stroke in Rats", Stroke, 32(11):2682-8.
Lu et al., 2002, "Intravenous Administration of Human Umbilical Cord Blood Reduces Neurological Deficit in the Rat After Traumatic Brain Injury", Cell Transplant, 11(3):275-81.
Lu, et al., 1996, "Stem Cells from Bone Marrow, Umbilical Cord Blood and Peripheral Blood for Clinical Application: Current Status and Future Application", Crit. Rev. Oncol. Hematol, 22:61-78.
Sanchez-Ramos, et al., 2001, "Expression of Neural Markers in Human Umbilical Cord Blood", Exp. Neur., 171:109-115.
Saporta et al., 2003, "Human Umbilical Cord Blood Stem Cells Infusion in Spinal Cord Injury: Engraftment and Beneficial Influence on Behavior", J. Hematotherapy & Stem Cell Research, 12:271-278.
Vendrame, et al., 2004, "Infusion of human umbilical cord blood cells in a rat model of stroke dose-dependently rescues behavioral deficits and reduces infarct volume", Stroke, 35(10):2390-5.
Willing et al., 2003, "Intravenous Versus Intrastriatal Cord Blood Administration in a Rodent Model of Stroke", J. Neuroscience Research, 73:296-307.
Zigova, et al., 2002, "Human Umbilical Cord Blood Cells Express Neural Antigens after Transplantation into the Developing Rat Brain", Cell Transplantation, 11:265-274.

* cited by examiner

*Primary Examiner*—Daniel E. Kolker
(74) *Attorney, Agent, or Firm*—Robert Varkonyi; Smith & Hopen, P.A.

(57) ABSTRACT

The present invention provides compositions and methods for enhancing the neuroprotective effect of umbilical cord blood cells. More particularly, the present invention provides methods of treating neurodegenerative disorders by administering umbilical cord blood cells and a substance capable of permeabilizing the blood brain barrier. In one embodiment, the blood brain barrier permeabilizer is mannitol. In another embodiment, the blood brain barrier permeabilizer is Cereport.

20 Claims, 5 Drawing Sheets

METHODS FOR ENHANCING NEUROPROTECTION VIA ADMINISTRATION OF STEM CELLS AND BLOOD BRAIN BARRIER PERMEABILIZERS

CROSS REFERENCE TO RELATED APPLICATIONS

The present invention claims the priority benefit of U.S. Provisional Patent Application Ser. No. 60/529,689, filed Dec. 15, 2003, and U.S. Provisional Patent Application Ser. No. 60/531,227, filed Dec. 19, 2003, the entire contents of which are hereby incorporated by reference.

BACKGROUND OF THE INVENTION

1. Field of the Invention

The field of this invention is the treatment of neurodegenerative disorders using stem cells. More specifically, the HUCB cell is administered to the individual in need of treatment along with a substance that permeabilizes the blood brain barrier in order to enhance the neuroprotective effect of the stem cells.

2. Background Art

Cerebrovascular disease, considered one of the top five non-communicable diseases, affects approximately 50 million people worldwide, resulting in approximately 5.5 million deaths per year. Of those 50 million, stroke accounts for roughly 40 million people. Stroke is the third leading cause of death in developed countries and accounts for the major cause of adult disability.

Stroke treatment consists of two categories: prevention and acute management. Prevention treatments currently consist of antiplatelet agents, anticoagulation agents, surgical therapy, angioplasty, lifestyle adjustments, and medical adjustments. An antiplatelet agent commonly used is aspirin. The use of anticoagulation agents seems to have no statistical significance. Surgical therapy appears to be effective for specific sub-groups. Angioplasty is still an experimental procedure with insufficient data for analysis. Lifestyle adjustments include quitting smoking, regular exercise, regulation of eating, limiting sodium intake, and moderating alcohol consumption. Medical adjustments include medications to lower blood pressure, lowering cholesterol, controlling diabetes, and controlling circulation problems.

Acute management treatments consist of the use of thrombolytics, neuroprotective agents, Oxygenated Fluorocarbon Nutrient Emulsion (OFNE) Therapy, Neuroperfusion, GPIIb/IIIa Platelet Inhibitor Therapy, and Rehabilitation/Physical Therapy.

A thrombolytic agent induces or moderates thrombolysis, and the most commonly used agent is tissue plasminogen activator (t-PA). Recombinant t-PA (rt-PA) helps reestablish cerebral circulation by dissolving (lysing) the clots that obstruct blood flow. It is an effective treatment, with an extremely short therapeutic window; it must be administered within 3 hours from onset. It also requires a CT scan prior to administration of the treatment, further reducing the amount of time available. Genetech Pharmaceuticals manufactures ACTIVASE® and is currently the only source of rt-PA.

Neuroprotective agents are drugs that minimize the effects of the ischemic cascade, and include, for example, Glutamate Antagonists, Calcium Antagonists, Opiate Antagonists, GABA-A Agonists, Calpain Inhibitors, Kinase Inhibitors, and Antioxidants. Several different clinical trials for acute ischemic stroke are in progress. Due to their complementary functions of clot-busting and brain-protection, future acute treatment procedures will most likely involve the combination of thrombolytic and neuroprotective therapies. However, like thrombolytics, most neuroprotectives need to be administered within 6 hours after a stroke to be effective.

Oxygenated Fluorocarbon Nutrient Emulsion (OFNE) Therapy delivers oxygen and nutrients to the brain through the cerebral spinal fluid. Neuroperfusion is an experimental procedure in which oxygen-rich blood is rerouted through the brain as a way to minimize the damage of an ischemic stroke. GPIIb/IIIa Platelet Inhibitor Therapy inhibits the ability of the glycoprotein GPIIb/IIIa receptors on platelets to aggregate, or clump. Rehabilitation/Physical Therapy must begin early after stroke, however, they cannot change the brain damage. The goal of rehabilitation is to improve function so that the stroke survivor can become as independent as possible.

Although some of the acute treatments showed promise in clinical trials, a study conducted in Cleveland showed that only 1.8% of patients presenting with stroke symptoms even received the t-PA treatment (Katzan IL, et al., 2000 JAMA, 283:1151-1158). t-PA is currently the most widely used of the above-mentioned acute stroke treatments, however, the number of patients receiving any new "effective" acute stroke treatment is estimated to be under 10%. These statistics show a clear need for the availability of acute stroke treatment at greater than 24 hours post stroke.

For some of these acute treatments (i.e., t-PA) the time of administration is crucial. Recent studies have found that the average time of arrival at the hospital is between 3 and 6 hours after stroke (Evenson et al., 2001 Neuroepidemiology, 20(2): 65-76.) t-PA has been shown to enhance recovery of ~⅓ of the patients that receive the therapy, however a recent study mandated by the FDA (Albers et al., 2000 JAMA, 283(9):1145-50.) found that about a third of the time the three-hour treatment window was violated resulting in an ineffective treatment. With the exception of rehabilitation, the remaining acute treatments are still in clinical trials and are not widely available in the U.S., particularly in rural areas, which may not have large medical centers with the needed neurology specialists and emergency room staffing, access to any of these new methods of stroke diagnosis and therapy may be limited for some time.

The cost of stroke in the US is over $43 billion, including both direct and indirect costs. The direct costs account for about 60% of the total amount and include hospital stays, physicians' fees, and rehabilitation. These costs normally reach $15,000/patient in the first three months; however, in approximately 10% of the cases, the costs are in excess of $35,000. Indirect costs account for the remaining portion and include lost productivity of the stroke victim, and lost productivity of family member caregivers.

Approximately 750,000 strokes occur in the U.S. every year, of which about ⅓ are fatal. Of the remaining patients, approximately ⅓ is impaired mildly, ⅓ is impaired moderately, and ⅓ is impaired severely. Ischemic stroke accounts for 80% of these strokes.

As the baby-boomers age, the total number of strokes is projected to increase substantially. The risk of stroke increases with age. After age 55, the risk of having a stroke doubles every decade, with approximately 40% of individuals in their 80's having strokes. Also, the risk of having a second stroke increases over time. The risk of having a second stroke is 25-40% five years after the first. With the over-65 portion of the population expected to increase as the baby boomers reach their golden years, the size of this market will grow substantially. Also, the demand for an effective treatment will increase dramatically.

Given the inability to effectively mitigate the devastating effects of stroke, it is imperative that novel therapeutic strategies are developed to both minimize the initial neural trauma as well as repair the damage brain once the pathological cascade of stroke has run its course.

Transplantation of stem cells has been proposed as a means of treating stroke. Neural stem cells are important treatment candidates for stroke and other CNS diseases because of their ability to differentiate in vitro and in vivo into neurons, astrocytes and oligodendrocytes. The powerful multipotent potential of stem cells may make it possible to effectively treat diseases or injuries with complicated disruptions in neural circuitry, such as stroke where more than one cell population is affected.

Despite this great potential, an easily obtainable, abundant, safe, and clinically proven source of stem cells has been elusive until recently. Umbilical cord blood contains a relatively high percentage of hematopoietic stem cells capable of differentiating into all of the major cellular phenotypes of the CNS, including neurons, oligodendrocytes, and glial cells (Sanchez-Ramos et al., 2001 Exp Neurol., 171(1):109-15; Bicknese et al., 2002 Cell Transplant, 11(3):261-4). Following intravenous delivery, human umbilical cord blood (HUCB) cells survive and migrate into the CNS of normal and diseased animals and have been shown to promote functional recovery in animal models of stroke, spinal cord injury, and hemorrhage (Chen et al., 2001 Stroke, 32(11):2682-8; Lu et al., 2002 Cell Transplant, 11(3):275-81; Saporta et al., 2003 J. Hematotherapy & Stem Cell Research, 12:271-278).

In addition to the growing body of evidence supporting the neurotherapeutic potential of HUCB cells, there is a long and well-established series of practical advantages of using HUCB for clinical diseases. Cord blood is easily obtained with no risks to the mother or child. A blood sample is taken from the umbilical vein attached to the placenta after birth. The percentage of the primitive stem cells present in the mononuclear fraction is small, but the absolute yield of stem cells available may number in the thousands prior to expansion or other ex vivo manipulation, providing an easily obtainable and plentiful source. Hematopoietic stem cells from HUCB have been routinely and safely used to reconstitute bone marrow and blood cell lineages in children with malignant and nonmalignant diseases after treatment with myeloablative doses of chemoradiotherapy (Lu et al., 1996 Crit Rev Oncol Hematol., 22(2):61-78; Broxmeyer, *Cellular characteristics of cord blood and cord blood transplantation.*, in AABB Press. 1998: Bethesda). Early results indicate that a single cord blood sample provides enough hematopoietic stem cells to provide both short- and long-term engraftment. This suggests that these stem cells maintain extensive replicative capacity, which may not be true of hematopoietic stem cells obtained from the adult bone marrow.

In addition, HUCB cells can also be easily cryopreserved following isolation. Cryopreservation of HUCB cells, accompanied by sustained good cell viability after thawing, also allows long-term storage and efficient shipment of cells from the laboratory to the clinic. Thus, this novel feature of cryopreservation gives HUCB a commercially distinct advantage in the design of cell-based therapeutic products. Although the duration of time that the cells may be stored with high viability upon thawing remains to be determined, it has been reported that HUCB cells may be frozen for at least 15 years, viable cells thawed, and transplanted within animal models of injury (Broxmeyer et al., 2003 Proc Natl Acad Sci USA., 100(2):645-650).

Because HUCB transplant recipients exhibit a low incidence and severity of graft-versus-host disease (Wagner et al., 1992 Blood, 79(7):1874-81; Gluckman et al., 1997 N Engl J. Med., 337(6): 373-81), long-term immune suppression with its associated health risks may be unnecessary, making HUCB an ideal candidate for cell-based products. Furthermore, as the technology for banking cord blood stem cells improves, it is possible that autologous transplantation (i.e., transplantation of an individual's own cells back into the body) will be plausible. This would completely eliminate the need for immune suppression during cellular therapy.

Intravenously administered HUCB cells preferentially survive and differentiate into neurons in the damaged brain, and promote behavioral recovery in preclinical models of stroke. While intravenous delivery of HUCB cells clearly promotes functional recovery in pre-clinical models of stroke, the behavioral improvements are only partial, leaving significant room for increments in the efficacy of these cells.

It has been previously recognized that the blood-brain barrier regulates entry of many blood-borne substances into the brain, and may exclude potentially therapeutic agents from entering the brain. Recently, Cornford & Cornford proposed that large neurotherapeutic molecules can be conjugated to peptidomimetic ligands, which bind to selected peptide receptors and are internalized in pinocytotic vesicles and thus cross the blood-brain barrier (Cornford & Cornford, 2002 Lancet Neurol., 1(5):306-15.) Others have proposed endovascular restorative neurosurgery as a novel method of inserting therapeutic agents into the brain, which avoids a craniotomy and allows the therapeutic agent to cross the blood brain barrier (Amar et al., 2003 Neurosurgery, 52(2):402-12). The transvascular route of delivery to the brain allows for the therapeutic molecules to cross the blood-brain barrier, and allows for widespread drug delivery to the brain (Pardridge, 2002 Neuron, 36(4):555-8). Alternatively, the blood-brain barrier can be completely avoided by inserting cellular implants into the CNS area of interest whereby the implant produces and releases therapeutic molecules directly into the CNS, such as by the encapsulation and insertion of xenogeneic cells within a selectively permeable polymeric membrane (Emerich & Winn, 2001 Crit Rev Ther Drug Carrier Syst., 18(3):265-98; Emerich & Salzberg, 2001 Cell Transplant, 10(1):3-24). However, none of these methods adequately addresses enhancing the neuroprotective effects observed with umbilical cord blood cells.

Because of the difficulty in effectively treating patients with neurological disorders, especially using cell-based therapies, there is a need in the art for methods and compositions to enhance the treatment of modalities.

SUMMARY OF THE INVENTION

It is an object of the present invention to overcome, or at least alleviate, one or more of the difficulties or deficiencies associated with the prior art. In that regard, the present invention provides methods and compositions to enhance the neuroprotective effects of stem cell treatment in a neurodegenerative disorder.

In that regard, the present invention fulfills in part the need to identify new, unique methods for treating cerebral ischemia.

In one embodiment, the method comprises administering cells obtained from umbilical cord blood to an individual in need of treatment, wherein the cells are administered systemically to the individual, and wherein a blood brain barrier permeabilizer is co-administered with the cells. In one embodiment, the cells obtained from human umbilical cord blood comprise a volume reduced cord blood sample. In a further embodiment, the cells obtained from human umbilical cord blood comprise an effective amount of a mononucleated cell.

The present invention further provides for a composition for the treatment of a neurodegenerative disorder. Preferably the neurodegenerative disorder is ischemia, and more preferably, a cerebral infarct. In one embodiment, the composition comprises an effective amount of cell obtained from umbilical cord blood and an effective amount of a blood brain barrier permeabilizer. In a further embodiment, the umbilical cord blood cell is a human umbilical cord blood cell. In one embodiment, the cells obtained from human umbilical cord blood comprise a volume reduced cord blood sample. In a further embodiment, the cells obtained from human umbilical cord blood comprise an effective amount of a mononucleated cell.

In embodiments of the present invention, the blood brain barrier permeabilizer is selected from the group consisting of mannitol; small fat-soluble molecules such as ethanol or ethanol derivatives; and water-soluble molecules such as glucose, mannitol, amino acids, dihydroxyphenylalanine, choline, and purine bases and nucleosides or derivatives thereof. However, other blood brain barrier molecules can be used that are known to those of ordinary skill in the art. In a preferred embodiment, the blood brain barrier permeabilizer is mannitol. In another preferred embodiment, the blood brain barrier permeabilizer is Cereport.

BRIEF DESCRIPTION OF THE DRAWINGS

FIG. 2B shows an analysis of neurotrophic factors in the brains of stroke animals that were not treated with HUCB cells. No significant elevations in the brain levels of neurotrophic factors were observed in animals that were treated with HUCB cells that had been previously treated with antibodies to neurotrophic factors. FIG. 2C shows an ELISA revealing that IA HUCB+mannitol increased GDNF brain levels at 3 days post-stroke. These increases were blocked when the HUCB cells were treated with neurotrophic factor antibody.

DETAILED DESCRIPTION OF THE INVENTION

Figure 1:
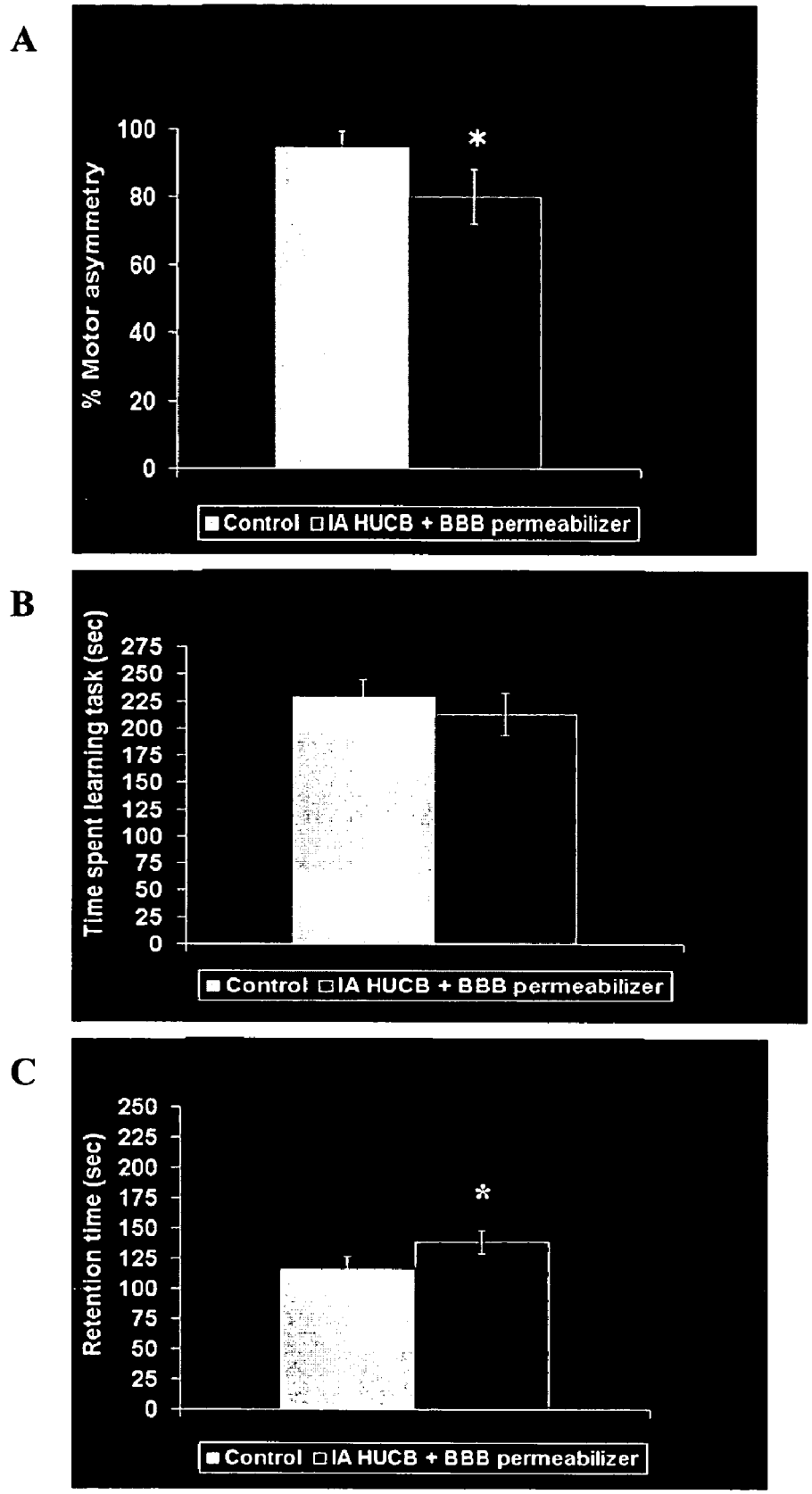
FIGS. 1A-C depict a behavioral profile of stroke animals. Stroke animals treated with intra-arterial HUCB+mannitol displayed significantly reduced motor asymmetry (A) in the EBST and decreased acquisition time (B) and increased retention time (C) in the passive avoidance task at day 3 after stroke compared with animals treated with intra-arterial vehicle alone (Vehicle).

The present invention provides methods and compositions to enhance the neuroprotective effects of stem cell treatment in a neurodegenerative disorder. Preferably, the neurodegenerative disorder is cerebral ischemia. To test the efficacy of enhancing neuroprotection using HUCB cells, HUCB cells were administered systemically into a patient along with a blood brain barrier permeabilizer.

The invention is directed to a therapeutic composition an effective amount of cells obtained from human umbilical cord blood and an effective amount of a blood brain barrier permeabilizer. In one embodiment, the cells obtained from human umbilical cord blood comprise a volume reduced cord blood sample. In a further embodiment, the cells obtained from human umbilical cord blood comprise an effective amount of a mononucleated cell.

In another embodiment, the invention is directed towards a therapeutic composition comprising an effective amount of stem cells and an effective amount of a blood brain barrier permeabilizer. In certain embodiments of the foregoing, the stem cells are selected from the group consisting of embryonic stem cells and adult stem cells.

In an additional embodiment, the invention encompasses a therapeutic composition comprising an effective amount of cells and an effective amount of a blood brain barrier permeabilizer. In certain embodiments, the cells are selected from the group consisting of blast cells, cloned cells, fertilized ova, placental cells, keratinocytes, basal epidermal cells, hair shaft cells, hair-root sheath cells, surface epithelial cells, basal epithelial cells, urinary epithelial cells, salivary gland cells, mucous cells, serous cells, von Ebner's gland cells, mammary gland cells, lacrimal gland cells, ceruminous gland cells, eccrine sweat gland cells, apocrine sweat gland cells, Moll gland cells, sebaceous gland cells, Bowman's gland cells, Brunner's gland cells, seminal vesicle cells, prostate gland cells, bulbourethral gland cells, Bartholin's gland cells, Littr gland cells, uterine endometrial cells, goblet cells of the respiratory or digestive tracts, mucous cells of the stomach, zymogenic cells of the gastric gland, oxyntic cells of the gastric gland, insulin-producing .beta. cells, glucagon-producing .alpha. cells, somatostatin-producing .delta. cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peripolar cells of the kidney, mesangial cells of the kidney, brush border cells of the intestine, striated duct cells of exocrine glands, gall bladder epithelial cells, brush border cells of the proximal tubule of the kidney, distal tubule cells of the kidney, nonciliated cells of ductulus efferens, epididymal principal cells, epididymal basal cells, hepatacytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroids plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood capillaries, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, megakaryocytes, monocytes, connective tissue macrophages, Langerhan's cells, osteoclasts, dendritic cells, microglial cells, neutrophils, eosinophils, basophils, mast cells, plasma cells, helper T cells, suppressor T cells, killer T cells, immunoglobulin M, immunoglobulin G, immunoglobulin A, immunoglobulin E, killer cells, rod cells, cone cells, inner hair cells of the organ of Corti, outer hair cells of the organ of Corti, type I hair cells of the vestibular apparatus of the ear, type II cells of the vestibular apparatus of the ear, type II taste bud cells, olfactory neurons, basal cells of olfactory epithelium, type I carotid body cells, type II carotid body cells, Merkel cells, primary sensory neurons specialized for touch, primary sensory neurons specialized for temperature, primary neurons specialized for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, oogonium, oocytes, spermatocytes, spermatogonium, ovarian follicle cells, Sertoli cells, and thymus epithelial cells, and combinations thereof. In a further composition, the cells are genetically modified.

In one embodiment, the composition is intended for systemic administration to an individual, although other methods for administration are contemplated. In one embodiment the effective amount of the mononucleated cell is approximately $1 \times 10^4$ to approximately $5 \times 10^7$ cells, more preferably is approximately $1 \times 10^5$ to approximately $9 \times 10^6$ cells, more preferably still is approximately $2 \times 10^5$ to approximately $8 \times 10^6$ cells, and most preferably is approximately $2 \times 10^5$ cells. In another embodiment, the effective amount of the mononucleated cell is approximately $0.1 \times 10^6$ cells/kg to approximately $10 \times 10^8$ cells/kg, more preferably is approximately $0.5 \times 10^6$ cells/kg to approximately $5 \times 10^8$ cells/kg, more preferably is approximately $1 \times 10^7$ cells/kg to approximately $2 \times 10^8$ cells/kg, more preferably is approximately $0.5 \times 10^8$ cells/kg, and most preferably is approximately $0.38 \times 10^8$ cells/kg.

The blood brain barrier permeabilizer is selected from the group consisting of mannitol, Cereport, small fat-soluble molecules, glucose, amino acids, dihydroxyphenylalanine, choline, and purine bases and nucleosides or derivatives thereof. Other blood brain barrier permeabilizers can be used that are known to those of ordinary skill in the art. In one embodiment, the blood brain barrier permeabilizer is mannitol. In another embodiment, the blood brain barrier permeabilizer is Cereport. In one embodiment, the concentration of mannitol is approximately 1.1 M. In other embodiments, mannitol is administered at a concentration of approximately 0.1 mol/L to approximately 10 mol/L, or at a concentration of approximately 0.5 mol/L to approximately 5 mol/L. In another embodiment, the concentration of Cereport is approximately 9 µg/kg. In other embodiments, Cereport is administered at a concentration of approximately 1 µg/kg to approximately 50 µg/kg, or at a concentration of approximately 5 µg/kg to approximately 20 µg/kg.

The invention is further directed to a method of treating a neurodegenerative disease, comprising administering an effective amount of cells obtained from human umbilical cord blood and an effective amount of a blood brain barrier permeabilizer to an individual with a neurodegenerative disease. In one embodiment, the cells obtained from human umbilical cord blood comprise a volume reduced cord blood sample. In a further embodiment, the cells obtained from human umbilical cord blood comprise an effective amount of a mononucleated cell. Preferably the individual is a human. In one embodiment, the mononucleated cell is frozen after being obtained from human umbilical cord blood and is thawed prior to administration to the individual.

It is contemplated that the neurodegenerative disease is selected from the group of diseases and injuries consisting of Parkinson's disease, Alzheimer's disease, multiple sclerosis, Tay Sach's disease, Rett Syndrome, lysosomal storage diseases, ischemia, cerebral infarct, spinal cord damage, ataxia, alcoholism, amyotrophic lateral sclerosis, schizophrenia and autism. In one embodiment, the neurodegenerative disease is ischemia or a cerebral infarct. In one method, the mononucleated cell is administered between approximately 15 minutes and 3 hours after the onset of the cerebral infarct, between approximately 15 minutes and 6 hours after the onset of the cerebral infarct, or between approximately 15 minutes and 12 hours after the onset of the cerebral infarct.

It is contemplated that treatment results in an increase in levels of a trophic factor in the circulating blood of the treated individual in comparison to the levels of trophic factors in an untreated individual with a cerebral infarct. In one embodiment the trophic factor is selected from the group consisting of GDNF, NGF, and BDNF. In a further embodiment, the trophic factor is GDNF.

It is further contemplated that treatment results in a decrease in cerebral infarct volume in comparison to the volume of a cerebral infarct in an untreated individual. In one embodiment, the volume is reduced by greater than approximately 10%, 15%, 20%, 21%, 22%, 23%, 24%, 25%, 26%, 27%, 28%, 29%, 30%, 31%, 32%, 33%, 34%, 35%, 36%, 37%, 38%, 39%, or 40%.

While it is contemplated that the blood brain barrier permeabilizer is administered to the individual at approximately the same time as the cells obtained from umbilical cord blood, the blood brain barrier permeabilizer may be administered in a separate composition from the cell. It is contemplated that the blood brain barrier permeabilizer may be administered prior to, simultaneously with, or after the administration of the cells obtained from umbilical cord blood. In addition, it is contemplated that the methods of the current invention may further comprise re-administering the blood brain barrier permeabilizer with or without the administration of further cells to the individual at approximately 3-72 hours after initial administration, or thereafter administered daily, weekly, monthly or yearly depending on the stroke outcome.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Abbreviations and nomenclature, where employed, are deemed standard in the field and commonly used in professional journals.

The umbilical cord blood cells of the subject invention can be administered to patients, including veterinary (non-human animal) patients, to alleviate the symptoms of a variety of pathological conditions for which cell therapy is applicable. For example, the cells of the present invention can be administered to a patient to alleviate the symptoms of neurological disorders or injuries such as cerebral ischemia or cerebral infarct; neurodegenerative diseases, such as Huntington's disease, Alzheimer's disease, and Parkinson's disease; traumatic brain injury; spinal cord injury; epilepsy; Tay Sach's disease; lysosomal storage diseases; amyotrophic lateral sclerosis; meningitis; multiple sclerosis and other demyelinating diseases; neuropathic pain; Tourette's syndrome; ataxia, drug addition, such as alcoholism; drug tolerance; drug dependency; depression; anxiety; and schizophrenia. In a preferred embodiment of the present invention, the cells are administered to alleviate the symptoms of cerebral ischemia or cerebral infarct.

The present invention is also directed to a method of treating neurological damage in the brain or spinal cord which occurs as a consequence of genetic defect, physical injury, environmental insult or damage from a stroke, heart attack or cardiovascular disease (most often due to ischemia) in a patient, the method comprising administering (including transplanting), an effective number or amount of umbilical cord blood cells to the patient, wherein a blood brain barrier permeabilizer is co-administered to the patient.

The present invention provides a novel method to enhance the neuroprotective effect seen by the administration of human umbilical cord blood cells without a blood brain barrier permeabilizer. These cells readily differentiate into various cells of the body, such as neuronal and glial cells, to be used in transplantation into a target site on or within the patient's body, such as the brain and spinal cord of a patient, e.g., for the treatment of neurodegenerative diseases. Optionally, the HUCB cells can be administered to a patient in a multipotent state or differentiated to varying degrees. Methods for differentiating HUCB cells are well known to those of ordinary skill in the art.

In one aspect of the present invention, cells obtained from HUCB are provided, which are suitable for administering systemically or to a target anatomical site along with a blood brain barrier permeabilizer. The cells obtained from HUCB can be grafted into a patient's brain or spinal cord, for example, or may be administered systemically, such as, but not limited to, intra-arterial or intravenous administration.

Pharmaceutical compositions of the present invention comprise cells obtained from HUCB in combination with an effective amount of at least one blood brain barrier permeabilizer. In a preferred embodiment, the blood brain barrier permeabilizer is selected from the group consisting of mannitol; small fat-soluble molecules such as ethanol or ethanol derivatives; and water-soluble molecules such as glucose, mannitol, amino acids, L-dopa (a naturally occurring amino acid, dihydroxyphenylalanine, found in broad beans), choline (an important part of acetylcholine and lecithin), purine bases and nucleosides or derivatives thereof. In one embodiment, the blood brain barrier permeabilizer is mannitol. In another preferred embodiment, the blood brain barrier permeabilizer is Cereport.

As used herein, the term "blood brain barrier permeabilizer" is a substance that is capable of disrupting the blood brain barrier. In one embodiment, the disruption is temporary. The amount of blood brain barrier permeabilizer administered with the umbilical cord blood cells is the amount effective to disrupt the blood brain barrier and allow neurotrophic growth factors to enter the brain in increased amounts and/or allow the cells obtained from HUCB to enter the brain. In one embodiment of the present invention, the blood brain barrier permeabilizer allows increased entry of neurotrophic factors into the brain when measured with 0-10 days after administration. In a further embodiment, the blood brain barrier permeabilizer does not allow an increased entry of cells obtained from HUCB into the brain when measured at 0-10 days after administration. In one embodiment, a brain barrier permeabilizer is selected and used such that at approximately 3 days after treatment, essentially no cells obtained from HUCB are detected in the central nervous system. As used herein, the term "essentially" refers to means that a de minimus number of cells obtained from HUCB are detected in the brain when administered with a blood brain barrier permeabilizer. For example, preferably less than 10%, more preferably less than 9%, more preferably less than 8%, more preferably less than 7%, more preferably less than 6%, more preferably less than 5%, more preferably less than 4%, more preferably less than 3%, more preferably less than 2%, or most preferably less than 1% of the cells administered systemically to the patient are detectable in the central nervous system at approximately 3 days after treatment, yet a neuroprotective effect is still observed.

In one embodiment, the administration of cells obtained from HUCB and a blood brain barrier permeabilizer leads to a measurable increase in the levels of neurotrophic factor in the brain of a patient when compared to the levels of neurotrophic factors in the absence blood brain barrier permeabilizer, or in the absence of any treatment. Preferably this increase is measurable at greater than approximately 24 hours after treatment or after stroke. In a further embodiment the increase is measurable at approximately 72 hours after treatment or after stroke. The neurotrophic factor may be any neurotrophic factor, including, but not limited to GDNF. In one embodiment, levels of GDNF in the treated brain are measurably increased at approximately 72 hours after stroke.

The compositions and methods of the present invention may be used for the treatment of stroke. Preferably the compositions and methods are utilized from immediately following stroke, up until approximately 28 days after stroke. In one preferred embodiment, the compositions and methods of the present invention are not limited in usage to the 3 hour post-stroke window that t-PA is limited to.

Preferably, a brain barrier permeabilizer is used that enhances the neuroprotective effects of cells obtained from HUCB. The neuroprotective effects may be determined in any way known now or later developed in the art to evaluate damage to the brain. For example, the neuroprotective effects of treatment may be evaluated using examining the histology of the brain, the behavior of the patient, or the size of the infarct may be examined using non-invasive techniques.

The pharmaceutical compositions may further comprise a neural cell differentiation agent. Neural cell differentiation agents for use in the present invention include for example, retinoic acid, fetal or mature neuronal cells including mesencephalic or striatal cells or a growth factor or cytokine such as brain derived neurotrophic factor (BDNF), glial derived neurotrophic factor (GDNF), glial growth factor (GFF), and nerve growth factor (NGF) or mixtures, thereof. Additional differentiation agents include, for example, growth factors such as fibroblast growth factor (FGF), transforming growth factors (TGF), ciliary neurotrophic factor (CNTF), bone-morphogenetic proteins (BMP), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, thrombopoietin, silencers, (including glial-cell missing, neuron restrictive silencer factor), antioxidants such as vitamin E (tocopherol) and vitamin E esters, among others including lipoic acid, SHC (SRC-homology-2-domain-containing transforming protein), neuroproteins, proteoglycans, glycoproteins, neural adhesion molecules, and other cell-signaling molecules and mixtures, thereof.

The pharmaceutical compositions may further comprise a pharmaceutically acceptable carrier.

The term "patient" is used herein to describe an animal, preferably a human, to whom treatment, including prophylactic treatment, with the cells according to the present invention, is provided. For treatment of those infections, conditions or disease states which are specific for a specific animal such as a human patient, the term patient refers to that specific animal. The term "donor" is used to describe an individual (animal, including a human) who or which donates umbilical cord blood or umbilical cord blood cells for use in a patient.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn. The use of umbilical cord blood as a source of mononuclear cells is advantageous because it can be obtained relatively easily and without trauma to the donor. In contrast, the collection of bone marrow cells from a donor is a traumatic experience. Umbilical cord blood cells can be used for autologous transplantation or allogenic transplantation, when and if needed. Umbilical cord blood is preferably obtained by direct drainage from the cord an/or by needle aspiration from the delivered placenta at the root and at distended veins. As used herein, the term "cells obtained from umbilical cord blood" refers to cells that are present within umbilical cord blood. In one embodiment, the cells obtained from umbilical cord blood are mononucleated cells that are further isolated from the umbilical cord blood using methods known to those of skill in the art. In a further embodiment, the umbilical cord blood cells may be further differentiated prior to administration to a patient. In another embodiment, the cells obtained from umbilical cord blood comprise a volume reduced cord blood sample. The production of a volume reduced cord blood sample is well-known to those of skill in the art. One non-limiting method for producing a volume reduced cord blood sample is adding Hespan in a 1:5 ratio to whole HUCB to the original collection bag, gently mixing the contents of the bag, and centrifuging the contents. After centrifugation, the blood bag is allowed to sit for 15 minutes in a closed plasma extractor. The buffy coat is transferred to a new Processing bag and centrifuged. The plasma is expressed and the remaining buffy coat is cooled for 15 minutes. A 50% DMSO: 5% Gentran 40 mixture is slowly added to the buffy coat and gently mixed. The cells are transferred to a Freezing bag and the cells are cryogenically frozen in a computer-controlled step down freezer. In further embodiments, the cells obtained from umbilical cord blood comprise cells that are effective for producing the intended result of treating a neurodegenerative disease.

The term "effective amount" is used herein to describe concentrations or amounts of components such as differentiation agents, umbilical cord blood cells, precursor or progenitor cells, specialized cells, such as neural and/or neuronal or glial cells, blood brain barrier permeabilizers and/or other agents that are effective for producing an intended result including differentiating stem and/or progenitor cells into specialized cells, such as neural, neuronal and/or glial cells, or treating a neurological disorder or other pathologic condition including damage to the central nervous system of a patient, such as a stroke, heart attack, or accident victim or for effecting a transplantation of those cells within the patient to be treated. Compositions according to the present invention may be used to effect a transplantation of the umbilical cord blood cells within the composition to produce a favorable change in the brain or spinal cord, or in the disease or condition treated, whether that change is an improvement such as stopping or reversing the degeneration of a disease or condition, reducing a neurological deficit or improving a neurological response, or a complete cure of the disease or condition treated.

The terms "stem cell" or "progenitor cell" are used interchangeably herein to refer to umbilical cord blood-derived stem and progenitor cells. The terms stem cell and progenitor cell are known in the art (e.g., Stem Cells: Scientific Progress and Future Research Directions, report prepared by the National Institutes of Health, June, 2001). The term "neural cells" are cells having at least an indication of neuronal or glial phenotype, such as staining for one or more neuronal or glial markers or which will differentiate into cells exhibiting neuronal or glial markers. Examples of neuronal markers that may be used to identify neuronal cells according to the present invention include, for example, neuron-specific nuclear protein, tyrosine hydroxylase, microtubule associated protein, and calbindin, among others. The term neural cells also includes cells which are neural precursor cells, i.e., stem and/or progenitor cells which will differentiate into or become neural cells or cells which will ultimately exhibit neuronal or glial markers, such term including pluripotent stem and/or progenitor cells which ultimately differentiate into neuronal and/or glial cells. All of the above cells and their progeny are construed as neural cells for the purpose of the present invention. Neural stem cells are cells with the ability to proliferate, exhibit self-maintenance or renewal over the lifetime of the organism and to generate clonally related neural progeny. Neural stem cells give rise to neurons, astrocytes and oligodendrocytes during development and can replace a number of neural cells in the adult brain. Neural stem cells are neural cells for purposes of the present invention. The terms "neural cells" and "neuronal cells" are generally used interchangeably in many aspects of the present invention. Preferred neural cells for use in certain aspects according to the present invention include those cells which exhibit one or more of the neural/neuronal phenotypic markers such as Musashi-1, Nestin, NeuN, class III β-tubulin, GFAP, NF-L, NF-M, microtubule associated protein (MAP2), S100, CNPase, glypican (especially glypican 4), neuronal pentraxin II, neuronal PAS 1, neuronal growth associated protein 43, neurite outgrowth extension protein, vimentin, Hu, internexin, O4, myelin basic protein and pleiotrophin, among others.

The term "administration" or "administering" is used throughout the specification to describe the process by which cells of the subject invention, such as mononucleated umbilical cord blood cells obtained from umbilical cord blood, volume reduced cord blood, or more differentiated cells obtained therefrom, are delivered along with a blood brain barrier permeabilizer to a patient for therapeutic purposes. Cells of the subject invention can be administered a number of ways including, but not limited to, parenteral (such term referring to intravenous and intra-arterial as well as other appropriate parenteral routes), intrathecal, intraventricular, intraparenchymal (including into the spinal cord, brainstem or motor cortex), intracisternal, intracranial, intrastriatal, and intranigral, among others which term allows cells of the subject invention to migrate to the ultimate target site where needed. Cells of the subject invention can be administered in the form of intact umbilical cord blood or a fraction thereof (such term including a mononuclear fraction thereof or a fraction of mononuclear cells, including a high concentration of stem or progenitor cells). The compositions according to the present invention may be used without treatment with a mobilization agent or differentiation agent ("untreated" i.e., without further treatment in order to promote differentiation of cells within the umbilical cord blood sample) or after treatment ("treated") with a differentiation agent or other agent which causes certain stem and/or progenitor cells within the umbilical cord blood sample to differentiate into cells exhibiting a differentiated phenotype, such as a neuronal and/or glial phenotype.

The umbilical cord blood stem or progenitor cells can be administered systemically or to a target anatomical site, permitting the cells to differentiate in response to the physiological signals encountered by the cell (e.g., site-specific differentiation). Alternatively, the cells may undergo ex vivo differentiation prior to administration into a patient.

Administration will often depend upon the disease or condition treated and may preferably be via a parenteral route, for example, intravenously, by administration into the cerebral spinal fluid or by direct administration into the affected tissue in the brain. For example, in the case of Alzheimer's disease, Huntington's disease, and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but may be directly into the affected tissue (which may be readily determined using MRI or other imaging techniques), or may be administered systemically. In a preferred embodiment of the present invention, the route of administration for treating an individual post-stroke is systemic, via intravenous or intra-arterial administration.

The terms "grafting" and "transplanting" and "graft" and "transplantation" are used throughout the specification synonymously to describe the process by which cells of the subject invention are delivered to the site where the cells are intended to exhibit a favorable effect, such as repairing damage to a patient's central nervous system (which can reduce a cognitive or behavioral deficit caused by the damage), treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Cells of the subject invention can also be delivered in a remote area of the body by any mode of administration as described above, relying on cellular migration to the appropriate area to effect transplantation. Preferably the cells are administered with a blood brain barrier permeabilizer.

The term "non-tumorigenic" refers to the fact that the cells do not give rise to a neoplasm or tumor. Stem and/or progenitor cells for use in the present invention are preferably free from neoplasia and cancer.

The term "differentiation agent" or "neural differentiation agent" is used throughout the specification to describe agents which may be added to cell culture (which term includes any cell culture medium which may be used to grow neural cells according to the present invention) containing umbilical cord blood pluripotent or multipotent stem and/or progenitor cells which will induce the cells to a more differentiated phenotype, such as a neuronal or glial phenotype. Preferred differentiation agents for use in the present invention include, for example, antioxidants, including retinoic acid, fetal or mature neuronal cells including mesencephalic or striatal cells or a growth factor or cytokine such as brain derived neurotrophic factor (BDNF), glial derived neurotrophic factor (GDNF) and nerve growth factor (NGF) or mixtures thereof. Additional differentiation agents include, for example, growth factors such as fibroblast growth factor (FGF), transforming growth factors (TGF), ciliary neurotrophic factor (CNTF), bone-morphogenetic proteins (BMP), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, thrombopoietin, silencers, (including glial-cell missing, neuron restrictive silencer factor), SHC(SRC-homology-2-domain-containing transforming protein), neuroproteins, proteoglycans, glycoproteins, neural adhesion molecules, and other cell-signaling molecules and mixtures, thereof. Differentiation agents which can be used in the present invention are detailed in "Marrow-mindedness: a perspective on neuropoiesis" by Bjorn Scheffler et al., *TINS*, 1999, 22:348-356, which is incorporated by reference herein in its entirety.

The term "neurodegenerative disease" is used herein to describe a disease which is caused by damage to the central nervous system and which damage can be reduced and/or alleviated through transplantation of neural cells according to the present invention to damaged areas of the brain and/or spinal cord of the patient. Exemplary neurodegenerative diseases which may be treated using the neural cells and methods according to the present invention include for example, Parkinson's disease, Huntington's disease, amyotrophic lateral sclerosis, Alzheimer's disease, Rett Syndrome, lysosomal storage diseases ("white matter disease" or glial/demyelination disease, as described, for example by Folkerth, *J. Neuropath. Exp. Neuro.*, September 1999, 58:9), including Sanfilippo, Gaucher disease, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. Neurodegenerative diseases also include neurodevelopmental disorders including for example, autism and related neurological diseases such as schizophrenia, among numerous others.

The term "gene therapy" is used throughout the specification to describe the transfer and stable insertion of new genetic information into cells for the therapeutic treatment of diseases or disorders. The foreign gene is transferred into a cell that proliferates to spread the new gene throughout the cell population. Thus, umbilical cord blood cells, or progenitor cells are the targets of gene transfer either prior to differentiation or after differentiation to a neural cell phenotype. The umbilical cord blood stem or progenitor cells of the present invention can be genetically modified with a heterologous nucleotide sequence and an operably linked promoter that drives expression of the heterologous nucleotide sequence. The nucleotide sequence can encode various proteins or peptides of interest. The gene products produced by the genetically modified cells can be harvested in vitro or the cells can be used as vehicles for in vivo delivery of the gene products (i.e., gene therapy).

The following written description provides exemplary methodology and guidance for carrying out many of the varying aspects of the present invention.

Molecular Biology Techniques

Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989). Polymerase chain reaction (PCR) is carried out generally as in PCR Protocols: A Guide to Methods and Applications, Academic Press, San Diego, Calif. (1990). Reactions and manipulations involving other nucleic acid techniques, unless stated otherwise, are performed as generally described in Sambrook et al., Molecular Cloning: A Laboratory Manual, Cold Springs Harbor Laboratory Press, and methodology as set forth in U.S. Pat. Nos. 4,666,828; 4,683,202; 4,801,531; 5,192,659; and 5,272,057 and incorporated herein by reference. In situ PCR in combination with Flow Cytometry can be used for detection of cells containing specific DNA and mRNA sequences (see, for example, Testoni et al., Blood, 1996, 87:3822).

Standard methods in immunology known in the art and not specifically described are generally followed as in Stites et al. (Eds.), Basic And Clinical Immunology, 8th Ed., Appleton & Lange, Norwalk, Conn. (1994); and Mishell and Shigi (Eds.), Selected Methods in Cellular Immunology, W.H. Freeman and Co., New York (1980).

Immunoassays

In general, immunoassays are employed to assess a specimen such as for cell surface markers or the like. Immunocytochemical assays are well known to those skilled in the art. Both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521 as well as Sambrook et al., Molecular Cloning: A Laboratory Manual, Cold Springs Harbor, N.Y., 1989. Numerous other references also may be relied on for these teachings.

Antibody Production

Antibodies may be monoclonal, polyclonal, or recombinant. Conveniently, the antibodies may be prepared against the immunogen or immunogenic portion thereof, for example, a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Springs Harbor, N.Y. (1988) and Borrebaeck, Antibody Engineering—A Practical Guide by W.H. Freeman and Co. (1992). Antibody fragments may also be prepared from the antibodies and include Fab and F(ab')2 by methods known to those skilled in the art. For producing polyclonal antibodies a host, such as a rabbit or goat, is immunized with the immunogen or immunogenic fragment, generally with an adjuvant and, if necessary, coupled to a carrier; antibodies to the immunogen are collected from the serum. Further, the polyclonal antibody can be absorbed such that it is monospecific. That is, the serum can be exposed to related immunogens so that cross-reactive antibodies are removed from the serum rendering it monospecific.

For producing monoclonal antibodies, an appropriate donor is hyperimmunized with the immunogen, generally a mouse, and splenic antibody-producing cells are isolated. These cells are fused to immortal cells, such as myeloma cells, to provide a fused cell hybrid that is immortal and secretes the required antibody. The cells are then cultured, and the monoclonal antibodies harvested from the culture media.

For producing recombinant antibodies, messenger RNA from antibody-producing B-lymphocytes of animals or hybridoma is reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system. Antibody cDNA can also be obtained by screening pertinent expression libraries. The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982). The binding of antibodies to a solid support substrate is also well known in the art. (see for a general discussion Harlow & Lane, Antibodies: A Laboratory Manual, Cold Spring Harbor Laboratory Publications, New York, 1988 and Borrebaeck, Antibody Engineering—A Practical Guide, W.H. Freeman and Co., 1992). The detectable moieties contemplated with the present invention can include, but are not limited to, fluorescent, metallic, enzymatic and radioactive markers. Examples include biotin, gold, ferritin, alkaline phosphates, galactosidase, peroxidase, urease, fluorescein, rhodamine, tritium, $^{14}$C, iodination and green fluorescent protein.

Gene Therapy

Gene therapy as used herein refers to the transfer of genetic material (e.g., DNA or RNA) of interest into a host to treat or prevent a genetic or acquired disease or condition. The genetic material of interest encodes a product (e.g., a protein, polypeptide, and peptide, functional RNA, antisense) whose in vivo production is desired. For example, the genetic material of interest encodes a hormone, receptor, enzyme polypeptide or peptide of therapeutic value. Alternatively, the genetic material of interest encodes a suicide gene. For a review see "Gene Therapy" in Advances in Pharmacology, Academic Press, San Diego, Calif., 1997.

Administration of Cells for Transplantation

The umbilical cord blood cells of the present invention can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art.

In the method of the present invention, the umbilical cord blood cells of the present invention can be administered in various ways as would be appropriate to implant in the central nervous system, including but not limited to parenteral, including intravenous and intraarterial administration, intrathecal administration, intraventricular administration, intraparenchymal, intracranial, intracisternal, intrastriatal, and intranigral administration. Preferably the umbilical cord blood cells are administered with a blood brain barrier permeabilizer, such as mannitol. Optionally, the umbilical cord blood cells and blood brain barrier permeabilizer are administered in conjunction with an immunosuppressive agent.

Pharmaceutical compositions comprising effective amounts of umbilical cord blood cells are also contemplated by the present invention. These compositions comprise an effective number of cells, optionally, in combination with a pharmaceutically acceptable carrier, additive or excipient. In certain aspects of the present invention, cells are administered to the patient in need of a transplant in sterile saline. In other aspects of the present invention, the cells are administered in Hanks Balanced Salt Solution (HBSS) or Isolyte S, pH 7.4. Other approaches may also be used, including the use of serum free cellular media. Systemic administration of the cells to the patient may be preferred in certain indications, whereas direct administration at the site of or in proximity to the diseased and/or damaged tissue may be preferred in other indications.

Pharmaceutical compositions according to the present invention preferably comprise an effective number within the range of about $1 \times 10^4$ cells to about $5 \times 10^7$ cells, more preferably about $1 \times 10^5$ to about $9 \times 10^6$ cells, even more preferably about $2 \times 10^5$ to about $8 \times 10^6$ cells generally in solution, optionally in combination with a pharmaceutically acceptable carrier, additive or excipient. In one embodiment about $2 \times 10^5$ cells are administered to the individual.

Preferably the umbilical cord blood cells are administered with a blood brain barrier permeabilizer. In one embodiment, the cells are combined with the permeabilizer prior to administration into the patient. In another embodiment, the cells are administered separately to the patient from the permeabilizer. Optionally, if the cells are administered separately from the permeabilizer, there is a temporal separation in the administration of the cells and the permeabilizer. The temporal separation may range from about less than a minute in time, to about hours or days in time. The determination of the optimal timing and order of administration is readily and routinely determined by one of ordinary skill in the art.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Permeabilization of the Blood Brain Barrier with Mannitol Enhances the Behavioral Effects of HUCB Transplantation The histological and neurobehavioral effects of early intracerebral and intra-arterial delivery of HUCB cells into rats during transient middle cerebral artery (MCA) occlusion were examined (Lobel et al., 2003 Exper. Neurol. 181: 97-98). Twenty-six adult male Sprague-Dawley rats were subjected to right MCA occlusion for 60 minutes. During the one-hour occlusion, animals were subjected to intra-arterial (IA) injection of HUCB (200,000 cells in 10 ul), with or without a blood brain barrier permeabilizer (1.1 M mannitol at 4° C.). Behavioral tests were conducted on post-stroke day 3, prior to sacrificing animals for histology to determine lesion volumes and HUCB cell survival. Separate sets of identically treated animals were used to measure brain levels of glial cell line-derived neurotrophic factor (GDNF), nerve growth factor (NGF), and brain-derived neurotrophic factor (BDNF) were measured by enzyme-linked immunosorbent assay (ELISA).

Methods

Animal care and housing: Animals were housed in pairs in polycarbonate cages with food and water available ad libitum in a temperature-controlled room (22° C.+/−3° C., 12 hour light-dark cycle). Following surgery, animals were placed in clean, warmed cages until they gaining consciousness, at which time they were returned to the animal colony room. Food and water were freely accessible at a lowered height in their cages. Animals were given antibiotics and analgesics for 3 days after surgery.

HUCB Collection: After delivery, the umbilical cord was double clamped as per normal standard of care. The umbilical cord was wiped with 70% alcohol and betadine at the needle insertion (collection) site, which was just proximal to the clamp that remains on the cord. The 16-gauge, ultra thin wall needle was inserted into the umbilical cord and held in place. The blood was allowed to flow into the attached collection bag, normally 3-5 minutes (the placenta & cord could be elevated slightly to increase the volume of blood collected) with ~50-100 mL collected. Once collection was complete, 2-3 knots were tied in the collection tubing to prevent leakage and the bag was gently inverted to mix the cord blood with citrate-phosphate-dextrose (CPD) anticoagulant. The collection bag was placed into a plastic bag and secured to the bottom of the collection kit container, which was then sealed. The sample was stored at 15°-25° C. until transported to Saneron CCEL Therapeutics, Inc. for processing.

HUCB Cell Preparation: Fresh umbilical cord blood was collected post-birth and processed within 48 hours of collection. Blood cell counts [nucleated, mononucleated, $CD34^+$, red blood, colony forming unit, granulocyte, monocyte, lymphocyte, and platelet cell counts (total count and percentage)] were taken prior to start of processing. Gradient separation of the mononucleated fraction (MNF) from the plasma was performed using Ficoll-hypaque at 400 g for 30 minutes. The MNF was collected and washed 3 times with RPMI-1640 (Gibco BRL). Blood cell counts were repeated and viability was determined. For this study, acceptable processed samples had $\geq 2 \times 10^7$ cells and $\geq 95\%$ viability. $10^7$ HUCB cells were placed in 1 mL of cryopreservation freezing media (90% Autologous Plasma, 10% DMSO). The HUCB cells were then cryogenically frozen in a computer-controlled step down freezer at a rate of −1° C./minute to −80° C. The HUCB cells were transferred to the vapor phase of liquid $N_2$. The cells remained in this cryogenic quarantine until results of the infectious disease testing were known (approximately 4 weeks).

MCA Occlusion surgical procedure: All surgical procedures were conducted under aseptic conditions. Anesthetized (equithesin 300 mg/kg i.p.) animals were subjected to the MCA occlusion model using a well-established embolic technique that occludes the right MCA. Based on prior studies (Borlongan et al., 1998 Exp Neurol., 149(2): 310-21; Borlongan et al., 1995 Physiol Behav., 58(5):909-17; Borlongan et al., 1995 Pharmacol Biochem Behav., 52(1):225-9), a one-hour occlusion of the MCA was observed to result in maximal infarction. In addition, the length (15-17 mm) and size of the tip (24-26 gauge) of the embolus were found to produce complete MCA occlusion in animals weighing between 250 and 350 g. A heating pad and a rectal thermometer allow maintenance of body temperature at normal limits. To ensure similar degree of stroke insults among animals, $PaO_2$, $PaCO_2$ and plasma pH measurements were monitored in each animal (Chang et al., 2000 Exp Neurol., 166(2):298-306). In addition, to ensure successful arterial occlusion, a Laser Doppler was used to monitor cerebral blood flow (Wang et al., 2001 Stroke, 32(3):775-82).

HUCB cell injection: The HUCB cells (provided by Saneron, Inc.) were thawed at 37° C. Cells were washed and centrifuged three times (1000 rpm for 7 minutes). Viability was determined using the trypan blue dye exclusion method and cell concentration was adjusted to 10,000 cells/µl. A minimum of 85% viability post-thaw was required for a sample to be used for transplantation. Immediately after the one-hour occlusion of the MCA, 200,000 HUCB cells, suspended in 10 µl solution in a 28-gauge Hamilton syringe, were injected intra-arterially using the same internal carotid artery where the embolic filament was previously inserted. Infusion rate was 1 µl per minute as determined by using a micro-infusion pump.

Behavioral testing: Stroke rats exhibit deficits in locomotor behavior and neurological functions, display motor asymmetry (i.e., since animals received unilateral MCAo, bias movements to one side of the body is displayed), and are impaired in cognitive performance (Borlongan et al., 1998 Exp Neurol., 149(2): 310-21; Borlongan et al., 1995 Physiol Behav., 58(5):909-17; Borlongan et al., 1995 Pharmacol Biochem Behav., 52(1):225-9; Borlongan et al., 1998 Neuroreport, 9(12):2837-42; Borlongan et al., 1998 Neuroreport, 9(16): 3703-9; Roof et al., 2001 Stroke, 32(11):2648-57). Thus, the present behavioral tests involve quantitative analyses of general locomotor behavior (using the Accuscan locomotor activity monitor apparatus), examination of neurological functions (Bederson test), semi-quantitative analysis of motor asymmetry (elevated body swing test, EBST), and quantitative analysis of performance in a cognitive task (step-down shuttle box passive avoidance test). The choice of weekly behavioral assessment was based on previous studies indicating that stroke symptoms become apparent as early as one week after stroke and are stable over a month and sustained up to at least 6 months post-stroke (Borlongan et al., 1998 Exp Neurol., 149(2): 310-21; Borlongan et al., 1995 Physiol Behav., 58(5):909-17; Borlongan et al., 1995 Pharmacol Biochem Behav., 52(1):225-9; Chang et al., 2000 Exp Neurol., 166(2):298-306; Borlongan et al., 1998 Neuroreport, 9(12):2837-42; Borlongan et al., 1998 Neuroreport, 9(16):3703-9; Roof et al., 2001 Stroke, 32(11):2648-57; Chiang et al., 1999 J Cereb Blood Flow Metab., 19(12):1329-35; Johnston et al., 2001 Brain Res., 900(2):268-76). These tests have been shown to be sensitive assays of behavioral deficits produced by unilateral MCAo stroke surgery (Aihara et al., 1994 Brain Res Bull., 33(5): 483-488; Borlongan et al., 1998 Exp Neurol., 149(2): 310-21; Borlongan et al., 1995 Physiol Behav., 58(5):909-17; Borlongan et al., 1995 Pharmacol Biochem Behav., 52(1):225-9; Roof et al., 2001 Stroke, 32(11):2648-57, Borlongan &. Sanberg, 1995 J. Neurosci., 15:5372-8; Nishino & Borlongan, 2000 Prog Brain Res., 127:461-76; Nishino et al., 1993 Brain Res Bull., 32:517-20). Animals were randomly subjected in the 4 tests mentioned above.

The Accuscan locomotor activity test is a sensitive behavioral test for determining the extent of MCAo-induced cerebral ischemia (Chang et al., 2003 Stroke, 34(2):558-64; Borlongan et al., 1995 Physiol Behav., 58(5):909-17; Borlongan et al., 1995 Pharmacol Biochem Behav., 52(1):225-9). For the Accuscan locomotor activity test, animals were tested at nighttime. The following locomotor variables were measured: horizontal activity, total distance, number of movements, movement time, rest time, speed, vertical activity, vertical movements, vertical time, stereotypy counts, number of stereotypes, stereotypy time, clockwise rotations and anticlockwise rotations. Data were collected every hour for 12 consecutive hours (6 PM to 6 AM).

The Bederson test is conducted following the procedures previously described (Altumbabic & Del Bigio, 1998 Neurosci Lett., 257(2):61-4). Neurologic score for each rat was obtained using 4 tests which include (1) observation of spontaneous ipsilateral circling, graded from 0 (no circling) to 3 (continuous circling); (2) contralateral hindlimb retraction, which measures the ability of the animal to replace the hindlimb after it is displaced laterally by 2 to 3 cm, graded from 0 (immediate replacement) to 3 (replacement after minutes or no replacement); (3) beam walking ability, graded 0 for a rat that readily traverses a 2.4-cm-wide, 80-cm-long beam to 3 for a rat unable to stay on the beam for 10 seconds; and (4) bilateral forepaw grasp, which measures the ability to hold onto a 2-mm-diameter steel rod, graded 0 for a rat with normal forepaw grasping behavior to 3 for a rat unable to grasp with the forepaws. The scores from all 4 tests, which were done over a period of about 15 minutes on each assessment day, were added to give a neurologic deficit score (maximum possible score, 12).

The EBST involves handling the animal by its tail and recording the direction of the swings. The test apparatus consisted of a clear Plexiglas box (40×40×35.5 cm). The animal was gently picked up at the base of the tail, and elevated by the tail until the animal's nose was at a height of 2 inches (5 cm) above the surface. The direction of the swing, either left or right, was counted once the animals head moved sideways approximately 10 degrees from the midline position of the body. After a single swing, the animal was placed back in the Plexiglas box and allowed to move freely for 30 seconds prior to retesting. These steps were repeated 20 times for each animal. Normally, intact rats display a 50% swing bias, that is, the same number of swings to the left and to the right. A 75% swing bias indicates 15 swings in one direction and 5 in the other during 20 trials. The EBST was previously utilized, and it was noted that MCAo stroke animals display >75% biased swing activity as early as the day of stroke surgery (i.e., after recovery from anesthesia), and such motor asymmetry is stable for up to six months (Borlongan et al., 1995 Physiol Behav., 58(5):909-17; Borlongan et al., 1995 Pharmacol Biochem Behav., 52(1):225-9).

Animals were introduced to passive avoidance testing as described in detail elsewhere (Borlongan et al., 1998 Neuroreport, 9(12):2837-42). Briefly, training and testing were carried out using a step-down passive avoidance box (27×27× 30 cm; Lafayette Inst. Co.) made of Plexiglas. A Plexiglas platform shelf (7.5×26.7×9.4 cm) is located in one corner of the box. Upon stepping off the platform, the rat received scrambled foot shock (approximately 2 mA; generated by a DC shock scrambler BRS Foringer No. SCS-003). Acquisition of the task is measured in terms of the amount of time it took the rat to remain on the platform continuously for 3 minutes. Twenty-four hours later, a retention test was conducted by placing the rat on the platform exactly as before and recording the latency to step-down measured to a maximum of 3 minutes. MCAo stroke animals display significant impairments in acquisition and retention of the task as early as 24 hours post-ischemia that persist at least up to 6 months post-ischemia (Chen et al., 2001 Stroke, 32(11):2682-8; Borlongan et al., 1998 Neuroreport, 9(16):3703-9).

Statistical analysis: The behavioral scores, number of surviving HUCB grafted cells and those expressing specific phenotypic markers, and infarct volumes were analyzed using ANOVA. The level of significances is set at <0.05. Post-hoc t-tests are performed for pair-wise comparisons of the different treatment conditions.

Results

Previous studies of the effects of HUCB in stroke demonstrated that behavioral recovery does not occur immediately but rather over a protracted, several-week period of time (Chen et al., 2001 Stroke, 32(11):2682-8; Willing et al., 2003 J. Neuroscience Research, 73:296-307). In the present studies, behavioral tests of both motor and cognitive function were conducted at a single early time point post stoke (i.e., day 3) to determine if combining HUCB cells with mannitol would produce more immediate and robust effects. While HUCB transplants alone were ineffective on all tests (i.e. no benefits were observed relative to animals receiving stroke only), combining HUCB cells with mannitol produced an impressive profile of behavioral recovery. Stroke-induced motor deficits, measured by percent motor asymmetry using the elevated swing bias test, were significantly reduced by 15% when HUCB cells were combined with mannitol and administered intra-arterially ($p<0.05$; FIG. 1A). Cognitive deficits measured by time to acquisition of a passive avoidance task showed a trend towards a reduction in acquisition time ($p=0.072$, FIG. 1B) and an analysis of memory of this same task revealed a significant 20% increase in retention time with intra-arterial administration ($p<0.05$) (FIG. 1C).

Example 2

Permeabilization of the Blood Brain Barrier with Mannitol Significantly Reduces Infarct Volume Following Stroke Animals were treated as described in Example 1.

Quantification of HUCB cell graft survival: 20 μm cryostat sectioned tissues were examined at 4× magnification and digitized using a PC-based Image Tools computer program. For estimation of surviving transplanted HUCB cells, sections were blind-coded and Abercrombie's formula was used to calculate the total number of NCAM-positive cells. Double-labeling of these human-specific antibodies with GFP provides unequivocal identification of HUCB cell grafts. Alternate brain sections were processed using antibodies directed against human neurons (NeuN), glia (GFAP), and oligodendrocytes (O-1) to reveal phenotypic differentiation of HUCB. Additional alternate brain sections were processed for Hematoxylin and Eosin to reveal the extent of cerebral damage. Cell counts were conducted to reveal the number of surviving HUCB grafted cells, the ratios of HUCB cells that differentiated into neurons, glia, and oligodendrocytes. Brain sections were blind-coded and Abercrombie's formula was used to calculate the total number of immunopositive cells (Borlongan et al., 2000 Neurosci Lett., 279(2):73-6; Borlongan et al., 1999 Cell Transplant., 8(1):153-9). Using an NIH imaging system, TTC staining was conducted to measure the maximum infarcted area in each animal. Infarct volume was calculated as 20 μm (thickness of the slice)×[sum of the infarction area in all brain slices ($\mu m^2$)] (Dillon-Arter et al., 2002 Cell Transplant, 11(3):251-9; Borlongan et al., 2003 Cell Transplant, 12(3):225-34).

Figure 4:
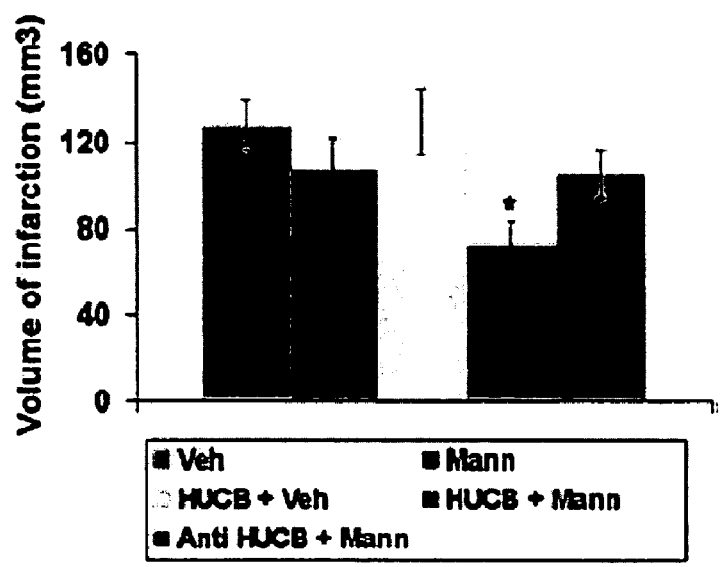
FIG. 4 depicts an analysis of infarct volume. TTC staining revealed that intravenous HUCB+mannitol (HUCB+Mann) significantly decreased stroke volumes compared with animals treated with intravenous vehicle alone (Veh), intravenous mannitol alone (Mann), or intravenous HUCB+vehicle (HUCB+Veh; *t tests; P<0.05). Pretreatment of HUCB with neutralizing antibodies (Anti-HUCB+Mann) prevented neuroprotection.

While behavioral recovery has been consistently reported using HUCB cells in stroke animals (Chen et al., 2001 Stroke, 32(11):2682-8; Willing et al., 2003 J. Neuroscience Research, 73:296-307), no report has yet suggested that HUCB transplants are capable of reducing infarct volume in those same animals. The studies of the current invention have shown that intra-arterial and intravenous delivery of HUCB during MCA occlusion also limited volume of infarcted tissue and promoted neuroprotection, but only when combined with mannitol (FIG. 4, showing treatment with IV HUCB+mannitol). Animals treated with HUCB cells and mannitol showed a statistically significant (p<0.05, ANOVA) 40% reduction in the size of infarction.

Example 3

Figure 3:
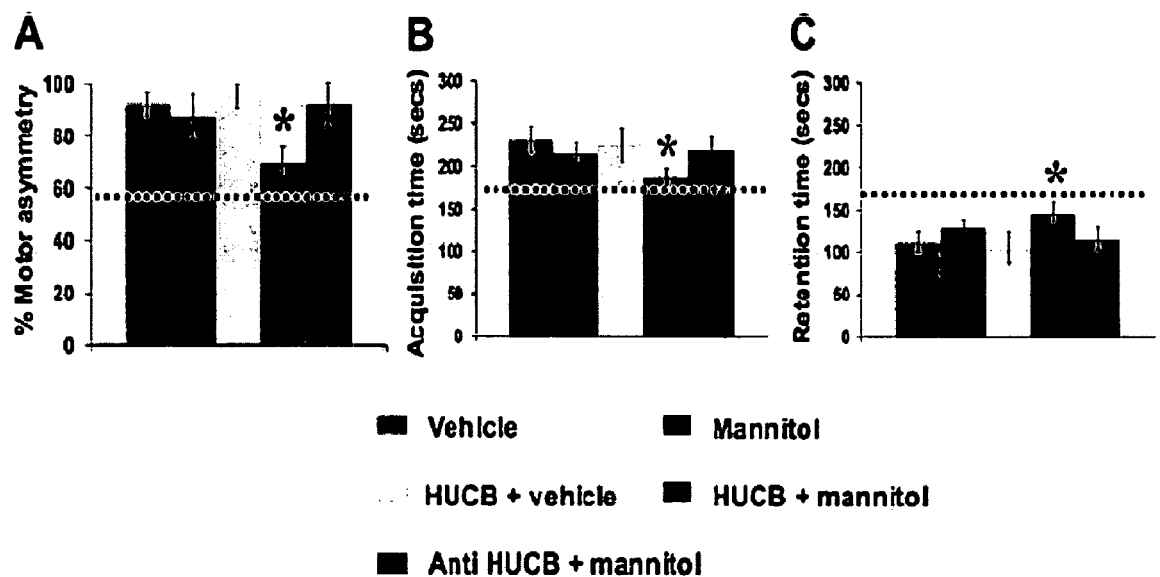
FIGS. 3A-C depict a behavioral profile of stroke animals. Stroke animals treated with intravenous HUCB+mannitol displayed significantly reduced motor asymmetry (A) in the EBST and decreased acquisition time (B) and increased retention time (C) in the passive avoidance task at day 3 after stroke compared with animals treated with intravenous vehicle alone (Vehicle), intravenous mannitol alone (Mannitol), or intravenous HUCB+vehicle (*t tests; P<0.05). However, they remained partially impaired compared with control animals (nonstroke, nontransplanted animals; dotted lines). Pretreatment of HUCB with neutralizing antibodies against GDNF, NGF, and BDNF (Anti HUCB+mannitol) blocked neuroprotection.

Permeabilization of the Blood Brain Barrier with Mannitol Significantly Increases Neurotrophic Activity The decrease in lesion volume 3 days after MCAo suggests that the HUCB cells are either exerting a direct trophic effect on the damaged tissue or are elevating endogenous levels of trophic activity. Replicating the above data, separate studies again confirmed that combining HUCB cells with mannitol produced a significant neuroprotective effect (FIGS. 3A-C). These studies also revealed associated elevations of brain levels of GDNF (increased 68% above controls, data not shown).

To confirm the potential involvement of trophic factors in the observed neuroprotection, one set of animals received MCAo plus HUCB and mannitol (n=12), while a second group of animals (n=20) were treated identically except that the HUCB cells were exposed to antibodies against NGF, GDNF and BDNF prior to transplantation. As anticipated, the elevations in GDNF levels were prevented (FIGS. 2B and 2C) and the behavioral and histological protective effects were completely blocked by pre-treatment of HUCB cells with antibodies to trophic factors. The observed increments in trophic factors, revealed by ELISA using anti-human monoclonal antibodies, were likely derived from the grafted HUCB cells, since the other treatments did not increase endogenous trophic factor levels.

Example 4

Permeabilization of the Blood Brain Barrier with Mannitol with Intravenous Administration of HUCB Cells Significantly Increases Neurotrophic Activity Adult male Sprague-Dawley rats were subjected to right MCA occlusion for 60 minutes. During the one-hour occlusion, animals were randomly assigned to one of the following treatments: intravenous (IV) injection of HUCB (200,000 cells in 10 µl) with blood brain barrier permeabilizer (1.1M mannitol at 4° C.; n=9) or vehicle (phosphate buffered saline, PBS; n=10), IV vehicle alone (n=8) or IV mannitol alone (n=8). An additional weight-matched group of adult male Sprague-Dawley rats (n=10) served as positive controls (i.e., non-stroke, non-transplanted, no drug treatment). Behavioral tests were conducted on post-stroke day 3 and thereafter, animals were euthanized for histological analysis of HUCB cell survival. HUCB cells were labeled with GFP using the lentiviral approach prior to transplantation to allow visualization of grafted cells. To reveal HUCB effects on cerebral infarcation, a new set of animals (n=10 per group) were subjected to the same treatment regimen.

While IV HUCB transplants alone were ineffective on all tests (i.e. no benefits were observed relative to animals receiving stroke only), combining HUCB cells with mannitol produced an impressive profile of behavioral recovery. Stroke-induced motor deficits, measured by percent motor asymmetry using the elevated swing bias test, were significantly reduced by 22% when HUCB cells were combined with mannitol ($F_{4,40}=39.81$, $p<0.05$). Cognitive deficits measured by time to acquisition of a passive avoidance task showed significant 16% reduction ($F_{4,40}=22.36$, $p<0.05$) in acquisition time and an analysis of memory of this same task revealed a significant 28% increase in retention time ($F_{4,40}=24.52$, $p<0.05$).

While behavioral recovery has been reported using HUCB cells in stroke animals, no report has yet demonstrated that HUCB transplants are capable of reducing infarct volume into those same animals. Here, IV HUCB during MCAo limited volume of infracted tissue, but only when combined with mannitol ($F_{3,36}=62.51$, $p<0.05$). Animals treated with HUCB cells and mannitol showed a statistically significant 40% reduction in the volume of infarction.

Immunohistochemical and GFP epiflourescence microscopy revealed no detectable IV HUCB cells in the brains of all animals at 3 days after stroke. To eliminate the possibility that lentivirally tagged-HUCB might have lost their human phenotype and GFP labeling after transplantation, parallel studies exposed stroke animals (n=20) to stereotaxic delivery of HUCB into the striatum and it was found that intraparenchymally grafted HUCB cells were positively labeled with human specific NCAM and GFP which persisted over long term post-transplantation (i.e., hours to 6 months of graft maturation). To check that HUCB cells might have entered at earlier periods after stroke and died during the disease progression, additional animals (n=30) were subjected to MCAo and received either IV HUCB plus vehicle of IV HUCB plus mannitol, then randomly sacrificed at 1, 2, 4, 8, 24, and 48 hours after stroke. These additional studies also revealed no detectable IV HUCB cells in the brain. Taken together, these results confirmed that peripherally administered HUCB cells did not cross the blood brain barrier with or without mannitol treatment.

Histologic examination of systemic organs at 3 days post-stroke revealed some human NCAM positive cells in kidneys, lungs and spleens, but not in the livers and hearts, in both transplant recipients of IV HUCB, with or without mannitol. Graft survival was not significantly different between these 2 groups. Thus, mere survival of HUCB cells in the peripheral organs of animals that did not receive mannitol was not enough to produce neuroprotection. H&E staining did not detect any tissue damage and tumor formation.

Figure 2:
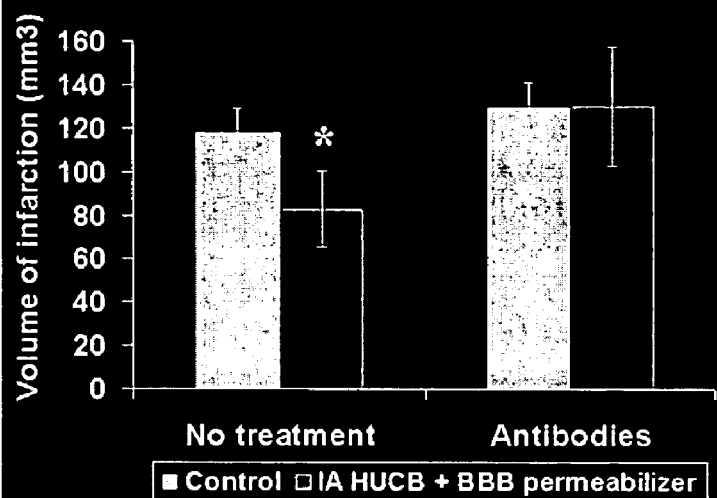
FIG. 2A depicts an analysis of infarct volume. IA HUCB cell grafts+mannitol significantly reduced the size of cerebral infarction compared to controls. However, pre-transplant exposure of HUCB cells to the neurotrophic factor antibody cocktail treatment, blocked the neuroprotective effects of HUCB cell grafts+mannitol.
FIGS. 2B and 2C show an analysis of neurotrophic factors.
Figure 2:
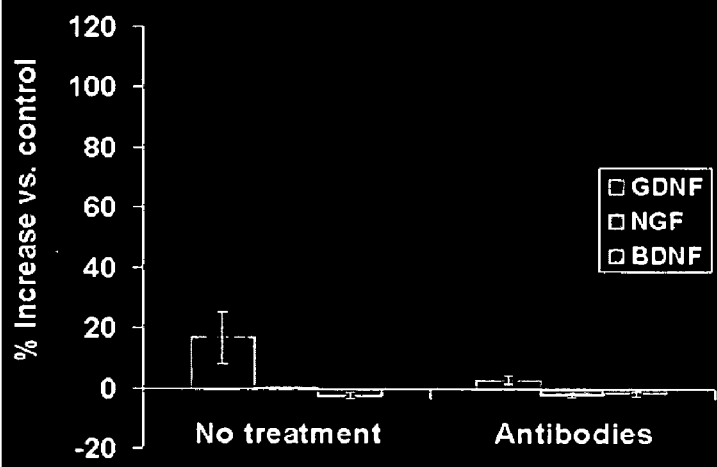
Figure 2:
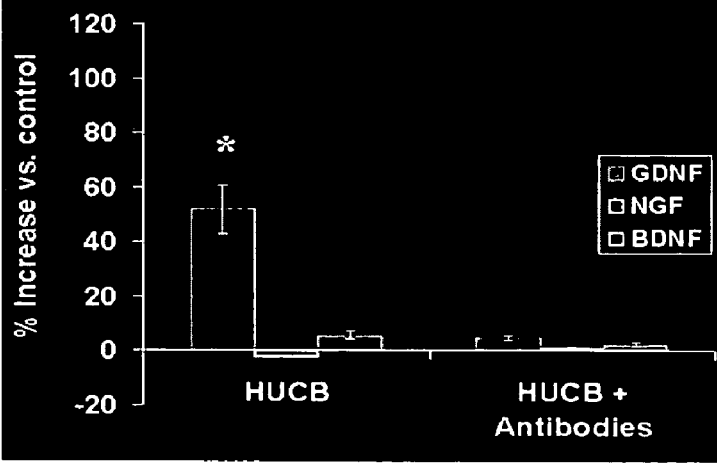
Figure 5:
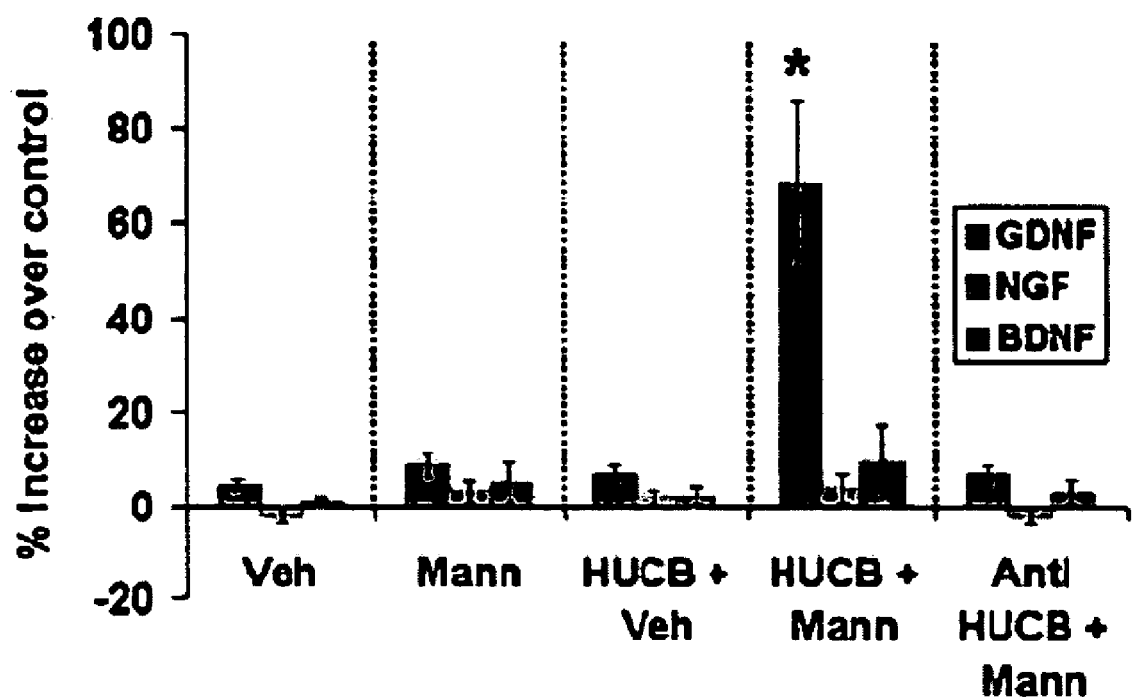
FIG. 5 shows an analysis of neurotrophic factors. ELISA revealed that intravenous HUCB+mannitol (HUCB+Mann) increased GDNF brain levels at day 3 after stroke compared with animals treated with intravenous vehicle alone (Veh), intravenous mannitol alone (Mann), or intravenous HUCB+vehicle (HUCB+Veh; *t tests; P<0.05). Pre-exposure of HUCB cells to neutralizing trophic factor antibodies prevented increments in GDNF brain levels.

In the absence of detectable HUCB cells in the brain, it was hypothesized that HUCB cells either exerted a direct trophic effect on the damaged tissue or elevated endogenous levels of trophic activity. Separate sets of identically treated animals (n=6 per treatment group: stroke then IV HUCB plus vehicle, IV HUCB plus mannitol, IV mannitol alone and IV vehicle alone) were used to measure brain levels of glial cell line-derived neurotrophic factor (GDNF), nerve growth factor (NGF), and brain-derived neurotrophic factor (BDNF) using enzyme-linked immunosorbent assay (ELISA). Replicating the above data, separate studies again confirmed that combining HUCB cells with mannitol produced a significant neuroprotective effect (FIG. 2). These studies also revealed associated elevations of brain levels of GDNF (increased 51% above controls; FIG. 5). Additional studies designed to determine the timing of elevations of trophic factors in stroke animals that received IV HUCB and mannitol, revealed increased brain levels of GDNF, NGF and BDNF at day 1, but only GDNF was sustained on subsequent days 2 and 3 post-stroke.

Finally, the blood levels of GDNF, NGF, and BDNF were measured to further determine the source of trophic factors. Additional stroke animals (n=6 per group) were subjected to the same surgical/drug regimen as above and were euthanized at day 3 after stroke. ELISA revealed low (15% above controls) but detectable levels of trophic factors from circulating blood in stroke animals that received intravenous HUCB grafts plus mannitol. In contrast, no detectable levels of trophic factors were obtained from stroke animals injected either with intravenous HUCB grafts alone, mannitol alone, or vehicle alone. The peripheral organs (kidneys, lungs, and spleens) were then assayed and GFP-labeled HUCB grafts were found, and significant elevations (125% to 160% above controls) were detected in trophic factors in stroke animals that received either the HUCB grafts plus mannitol or HUCB grafts alone compared with those that received mannitol alone or vehicle alone (non-significant increment of 8% above controls).

IV delivery of HUCB when combined with mannitol promoted neuroprotection with present low dose of 200,000 HUCB cells, which mimics those seen in other reports using much higher doses (>500,000 cells) of IV HUCB (Chen et al., 2001 Stroke, 32:2682-2688; Willing et al., 2003 Journal of Neuroscience Research, 73: 296-307).

In addition, while IV HUCB alone shows therapeutic effects when administered 24 hours to 7 days post injury (Chen et al., 2001 Stroke, 32:2682-2688; Willing et al., 2003 Journal of Neuroscience Research, 73: 296-307; Lu et al., 2002 Cell Transplant, 11:275-281), the addition of mannitol, which is used clinically for hyperosmolar therapy, allowed for the cells to be administered 3 hours after the injury. Although the delay in IV HUCB transplantation led to grafted cell visualization in the brain (Chen et al., 2001 Stroke, 32:2682-2688; Willing et al., 2003 Journal of Neuroscience Research, 73: 296-307), whereas the present early IV HUCB plus mannitol transplantation did not, both strategies produced neuroprotection. The advantage of early delivery of cells after stroke with adjunct mannitol is that an enhanced therapeutic effect, i.e. reduced cerebral infarction, was achieved. Finally, the present acute neuroprotection was induced without immunosuppression, which is generally requisite for long-term graft survival and often accompanied by deleterious side effects.

Example 5

Blood Brain Barrier Permeabilization Facilitates HUCB Cell Graft-Induced Motor and Cognitive Recovery in Stroke Animals Intravascular delivery of HUCB cells promotes behavioral recovery in rodent models of stroke, although the recovery is only partial (Chen et al., 2001 Stroke, 32(11):2682-8; Willing et al., 2003 J. Neuroscience Research, 73:296-307). Increasing the survival of HUCB cells in the CNS is correlated with behavioral recovery in several animal models of CNS diseases including stroke. Preliminary data indicates that co-administration of mannitol to permeabilize the blood brain barrier produces an immediate improvement (within 3 days) in behavioral recovery beyond that achieved with HUCB cells alone. Further studies confirm and extend those data by determining the extent to which mannitol augments the behavioral effects of HUCB transplants over a longer (1 month) period of time.

Methods

Rats initially undergo sham surgery (n=40) or stroke surgery (n=40). At 3 hours post-stroke, animals (n=10 per group) are randomly assigned to one of the following treatment conditions: (1) IV HUCB cells (200,000 viable cells) alone; (2) IV HUCB cells with mannitol (1.1 M mannitol at 4° C.); (3) IV mannitol alone, and; (4) IV vehicle alone. All animals will receive the immunosuppressant cyclosporin-A (10 mg/kg, i.p., daily throughout study period). Cyclosporin-A may exert neuroprotection on its own, thus an additional 10 stroke animals receive cyclosporin-A alone over the 28-day post-stroke period. Spontaneous activity (using an Accuscan activity monitor), neurologic (Bederson test), motor examination (elevated body swing test), and passive avoidance behavior are employed starting at 3, 7, 14 and 28 days post-stroke and are performed substantially as described in Example 1.

Results

Preliminary experiments demonstrated that intra-arterial delivery of HUCB cells restored behavioral function when combined with mannitol. While intra-arterial delivery is likely an effective means of achieving high concentrations of cells within the CNS, the use of this route may be a complicated and somewhat risky surgical procedure in the clinical setting. Intravenous delivery is markedly easier and still retains the ability to provide significant delivery to the CNS. The intravenous delivery route of delivering HUCB cells in combination with mannitol still produced significant behavioral effects relative to HUCB cells alone, as seen in Example 4.

If necessary, the numbers of HUCB cells are increased in subsequent trials until comparable effects are observed between the two groups at 28 days post-stroke. The behavioral benefits of combining HUCB cells with mannitol also increase over the 28-day testing period. Previous studies clearly support the contention that the functional effects of HUCB cells alone become greater over time. It is clinically important to determine the extent to which the effects of HUCB plus mannitol are both initially greater and continue to grow over time relative to that achieved with HUCB alone.

Example 6

Quantification of HUCB Cell Engraftment (Number of Surviving Cells) in Stroke Animals with and without Blood Brain Barrier Permeabilization Survival and engraftment of transplanted HUCB cells is a prerequisite for functional recovery following stroke. Indeed, the extent of behavioral recovery in animal models of stroke is dependant on the numbers of surviving HUCB within the damaged brain region. The present studies systematically quantify the ability of mannitol to further enhance HUCB cell engraftment and survival. By correlating enhanced cell survival with enhanced behavioral recovery these data provide essential preliminary dose-response information for the design of initial clinical trials in stroke patients.

Methods

Rats initially undergo sham surgery (n=40) or stroke surgery (n=40). At 3 hours post-stroke, animals (n=10 per group) are randomly assigned to one of the following treatment conditions: (1) IV HUCB cells (200,000 viable cells) alone; (2) IV HUCB cells with mannitol (1.1 M mannitol at 4° C.); (3) IV mannitol alone, and; (4) IV vehicle alone. All animals will receive the immunosuppressant cyclosporin-A (10 mg/kg, i.p., daily throughout study period). Cyclosporin-A may exert neuroprotection on its own, thus an additional 10 stroke animals receive cyclosporin-A alone over the 28-day post-stroke period. Animals are euthanized at 28 days post-stroke for quantitative analysis of surviving grafted HUCB cells. Lentiviral vector labeling of HUCB cells is used to initially identify the location of grafted cells (see lentiviral vector strategy below).

Lentiviral vector system: Lentiviruses were supplied by Dr. Didier Trono, and were grown further. This same lentivirus was demonstrated by Kordower and colleagues to be efficacious in delivery of GDNF, as well as promoting functional recovery in parkinsonian monkeys (Kordower et al., 2000 Science 290: 767-773). Preliminary data demonstrated that this strategy is successful in producing infectious viral particles expressing GFP in HUCB cells, in vitro and in vivo, i.e., following transplantation. This is the first use of lentivirus to manipulate GFP expression in HUCB cells. The procedures used were as described by Dr. Trono and colleagues in transfecting HUCB cells with the lentiviral vector (Lundberg et al., 2002 Neurol., 175(2):370-87). HUCB cells have been successfully labeled using the lentiviral vector system. Transduction efficiency was about 30%-35%, and was stable over 6 months following transplantation.

Immunohistochemistry: The rats are anesthetized with xylazine (13 mg/kg i.m.) and ketamine (44 mg/kg i.m.), then perfused with saline via a cardiac catheter followed by 3.0% paraformaldehyde. The brain is removed, placed into a rat brain matrix and sliced into 2 mm thick coronal sections. A small nick is made in the non-stroke side inferior cortex to facilitate maintenance of section orientation. The sections are immersion fixed overnight in 3% paraformaldehyde and then embedded in surgiplast formular-R. Paraffin-embedded sections are serially sectioned at 5 μM and mounted on superfrost plus slides (Fisher).

Alternatively, brains are perfused with saline followed by 1.5% paraformaldehyde and 0.1% glutaraldedyhe. The brains are immersion fixed for 3 hours in 1.5% paraformaldehyde and 0.1% glutaraldehyde then transferred to 20% sucrose in 1.5% paraformaldehyde and 0.1% glutaraldehyde at 4° C. overnight. The brain slices are snap frozen in OCT embedding compound using isopentane cooled by liquid nitrogen. Tissues are processed for immunohistochemistry using standard ABC method, a monoclonal antibody MOC-1 that recognizes a human-specific epitope in N-CAM and does not cross react with rodent N-CAM or other rodent proteins, is used to detect grafted HUCB cells in the rat brain (Borlongan et al., 1998 Neuroreport., 9(12):2837-42; Borlongan et al., 1998 Neuroreport., 9(16):3703-9).

Quantification of HUCB cell graft survival: 20 μm cryostat sectioned tissues are examined at 4× magnification and digitized using a PC-based Image Tools computer program. For estimation of surviving transplanted HUCB cells, sections are blind-coded and Abercrombie's formula is used to calculate the total number of NCAM-positive cells. Double-labeling of these human-specific antibodies with GFP provides unequivocal identification of HUCB cell grafts. Alternate brain sections are processed using antibodies directed against human neurons (NeuN), glia (GFAP), and oligodendrocytes (O-1) to reveal phenotypic differentiation of HUCB. Additional alternate brain sections are processed for Hematoxylin and Eosin to reveal the extent of cerebral damage. Cell counts are conducted to reveal the number of surviving HUCB grafted cells, the ratios of HUCB cells that differentiated into neurons, glia, and oligodendrocytes. Brain sections are blind-coded and Abercrombie's formula is used to calculate the total number of immunopositive cells (Borlongan et al., 2000 Neurosci Lett., 279(2):73-6, 2000; Borlongan et al., 1999 Cell Transplant., 8(1):153-9). Using an NIH imaging system, TTC staining is conducted to measure the maximum infarcted area in each animal. Infarct volume is calculated as 20 μm (thickness of the slice)×[sum of the infarction area in all brain slices ($\mu m^2$)] (Dillon-Arter et al., 2002 Cell Transplant, 11(3): 251-9; Borlongan et al., 2003 Cell Transplant, 12(3):225-34).

In addition, GFP epifluorescence is combined with immunohistochemistry using antibodies directed against human antigens. Dual labeling of cells with GFP and human antigen markers provides a definitive identification and delineation (from host rat tissue) of HUCB grafted cells. Surrogate immunocytochemical human markers (in addition to those noted in Example 7) will include NCAM and HO-14, human cell surface markers. Detailed immunohistochemical procedures and analyses are provided herein. The regions of analysis are the ipsilateral striatum, cortex and subcortex as these regions have previously been shown to be both the region of infarction as well as the location of the preponderance of engrafted HUCB cells. Additional tissue sections, not used in these studies, are saved for future analysis if needed.

Example 7

Reduction of Stroke Volume (i.e., Cerebral Infarction) is Enhanced in Stroke Animals that Receive HUCB Cell Grafts with Blood Brain Barrier Permeabilization Using cellular therapies to treat stroke hopefully minimizes initial trauma and facilitates subsequent repair processes. While HUCB cell transplants have consistently been shown to produce a gradual behavioral recovery that manifests over several weeks, no studies have yet reported any amelioration of the initial trauma. The preliminary data presented herein and elsewhere shows an amelioration of the initial trauma using HUCB cells alone. In addition, the data presented herein showed the combination of HUCB cells with mannitol produced a more rapid behavioral recovery (within 3 days) than previously reported. This unique combination significantly reduces infarct volume by as much as 30%. It is likely that both reducing lesion size and promoting repair of the damaged circuitry in stoke patients leads to greater efficacy than could be obtained with either phenomena alone.

Methods

Reduction of cerebral infarct is enhanced in stroke animals that receive HUCB cell grafts with blood brain barrier permeabilization. Alternate brain sections from Example 6 are processed for H&E and TTC and reveal the extent of cerebral damage. Brain sections throughout the region of infarct are used to calculate total lesion volume. The rationale for measuring stroke volume at 28 days post-transplantation is based on previous studies demonstrating that stable transplant-induced behavioral recovery is achieved at this period. Accordingly, if HUCB cell grafts plus mannitol possess beneficial effects, then reduction in cerebral infarction should be detected at 28 days post-transplantation.

Additionally, it is known that mannitol itself may reduce volume of infarction as seen in a few studies. Thus, a mannitol alone control group is used to delineate the possible neuroprotective effects of mannitol from HUCB cell graft plus mannitol treatment.

Example 8

Permeabilization of the Blood Brain Barrier with Cereport Enhances the Behavioral Effects of HUCB Transplantation The histological and neurobehavioral effects of early intra-arterial delivery of HUCB cells plus Cereport into rats during transient MCA occlusion were examined. Twenty-six adult male Sprague-Dawley rats were subjected to right MCA occlusion for 60 minutes. During the one-hour occlusion, animals were subjected to intra-arterial (IA) injection of HUCB (200,000 cells in 10 μl), with or without the BBB permeabilizer Cereport (9 μg/kg IV). The use of Cereport, offers certain advantages over mannitol in that Cereport produces a transient permeation of the blood brain barrier of only 15 minutes, and still retains a semi-permeable opening, allowing only 1 kD-size molecules in normal intact brain and 30-50 kD-size molecules in injured brain, which are novel features not well-characterized in mannitol.

Behavioral tests were conducted on post-stroke day 3, prior to sacrificing animals for histology to determine lesion volumes and HUCB cell survival. Separate sets of identically treated animals were used to measure brain levels of GDNF, NGF, and BDNF by ELISA. The histological observations paralleled the results seen with mannitol discussed supra.

Figure 6:
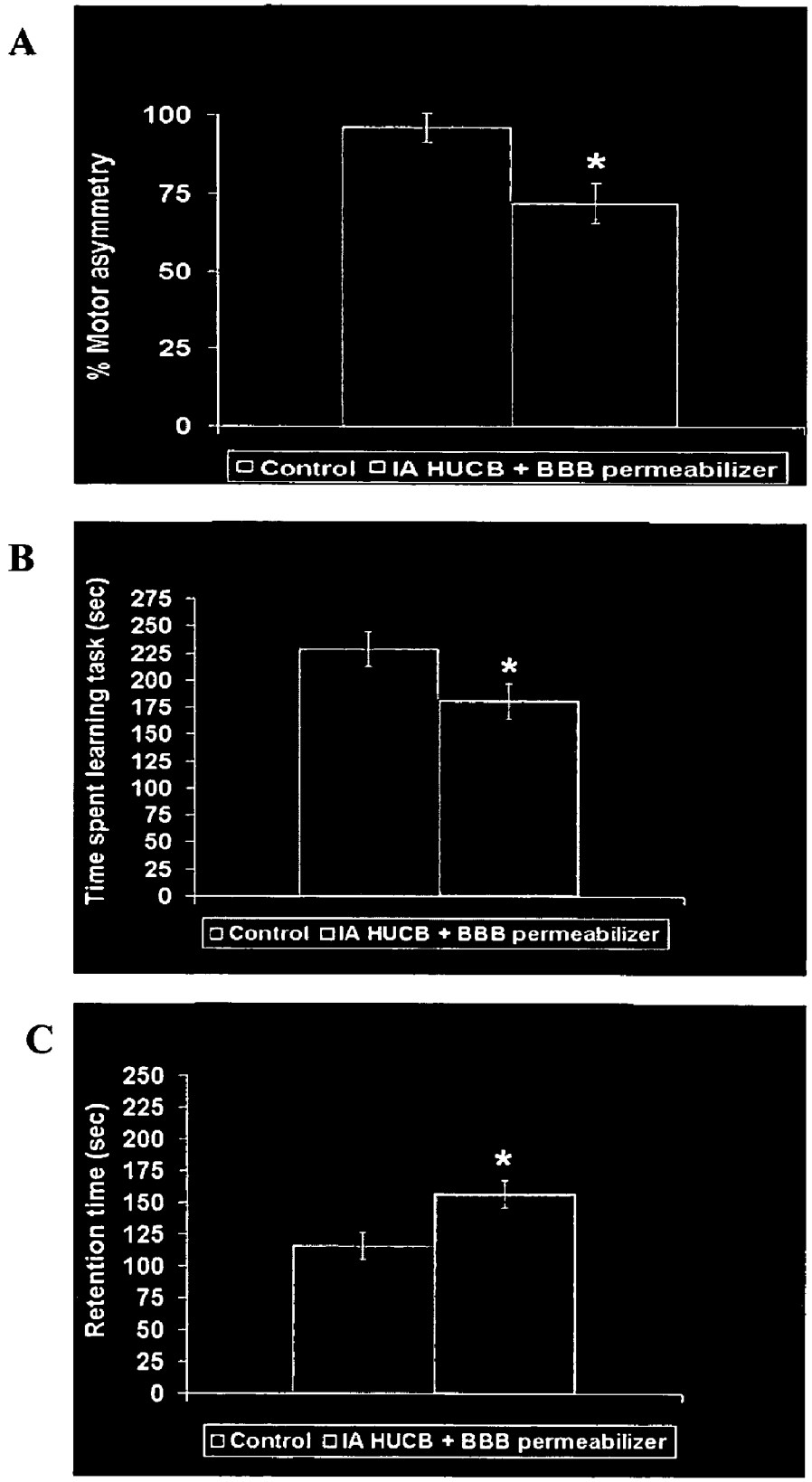
FIGS. 6A-C show treatment with intra-arterial HUCB cell grafts+Cereport significantly reduced stroke-induced motor asymmetry (A), and significantly produced a shorter acquisition time (B) and a longer retention time (C) on passive avoidance task than controls (HUCB alone or IA vehicle alone). In each panel, the control is shown on the left and IA HUCB+Cereport is shown on the right.

While HUCB transplants alone were ineffective on all tests, combining HUCB cells with Cereport produced an impressive profile of behavioral recovery. Stroke-induced motor deficits, measured by percent motor asymmetry using the elevated swing bias test, were significantly reduced by 25% when HUCB cells were combined with Cereport ($p<0.05$; FIG. 6A). Cognitive deficits, measured by time to acquisition of a passive avoidance task, showed a significant 20% reduction in acquisition time ($p<0.05$; FIG. 6B), and an analysis of retention time on this same test revealed a significant 30% increase in retention time ($p<0.05$) (FIG. 6C).

We claim:

1. A method of treating a neurodegenerative disease, comprising administering an effective amount of cells obtained from human umbilical cord blood and an effective amount of mannitol to an individual with a neurodegenerative disease.

2. The method of claim 1, wherein the neurodegenerative disease is selected from the group consisting of Parkinson's disease, Alzheimer's disease, multiple sclerosis, Tay Sach's disease, Rett Syndrome, lysosomal storage diseases, ischemia, spinal cord damage, ataxia, alcoholism, and amyotrophic lateral sclerosis.

3. The method of claim 1, wherein the neurodegenerative disease is ischemia.

4. The method of claim 1, wherein the neurodegenerative disease is a cerebral infarct.

5. The method of claim 1, wherein the individual is a human.

6. The method of claim 1, wherein the cells obtained from human umbilical cord blood comprise a volume reduced cord blood sample.

7. The method of claim 1, wherein mannitol is administered at a concentration of approximately 1.1 mol/L.

8. The method of claim 1, wherein the cells obtained from human umbilical cord blood comprise an effective amount of a mononucleated cell.

9. The method of claim 8, wherein the mononucleated cell is frozen after being obtained from human umbilical cord blood and is thawed prior to administration to the individual.

10. The method of claim 8, wherein the mononucleated cell is administered systemically.

11. The method of claim 8, wherein the neurodegenerative disease is a cerebral infarct.

12. The method of claim 11, wherein the mononucleated cell is administered up to 3 hours after the onset of the cerebral infarct.

13. The method of claim 11, wherein the mononucleated cell is administered between approximately 3 hours and 6 hours after the onset of the cerebral infarct.

14. The method of claim 11, wherein the mononucleated cell is administered between approximately 3 hours and 12 hours after the onset of the cerebral infarct.

15. The method of claim 8, wherein the effective amount of the mononucleated cell is approximately $1\times10^7$ cells/kg to approximately $2\times10^8$ cells/kg.

16. The method of claim 8, wherein the effective amount of the mononucleated cell is approximately $0.5\times10^8$ cells/kg.

17. The method of claim 8, wherein the effective amount of the mononucleated cell is approximately $0.38\times10^8$ cells/kg.

18. The method of claim 1, wherein the mannitol is administered to the individual separately from the mononucleated cell.

19. The method of claim 10, further comprising re-administering the mannitol to the individual at approximately 3-72 hours after initial administration.

20. The method of claim 19, wherein the mannitol is read-ministered with mononucleated cells.

* * * * *